United States Patent [19]

Sircar et al.

[11] Patent Number: 5,389,661

[45] Date of Patent: Feb. 14, 1995

[54] IMIDAZOLE AND 1,2,4-TRIAZOLE DERIVATIVES WITH ANGIOTENSIN II ANTAGONIST PROPERTIES

[75] Inventors: Ila Sircar, Ann Arbor, Mich.; Jagadish C. Sircar, Clarks Summit, Pa.

[73] Assignee: Warner-Lambert Company, Morris Plains, N.J.

[21] Appl. No.: 194,535

[22] Filed: Feb. 10, 1994

Related U.S. Application Data

[60] Division of Ser. No. 985,395, Dec. 4, 1992, Pat. No. 5,322,950, which is a continuation-in-part of Ser. No. 802,652, Dec. 5, 1991, abandoned.

[51] Int. Cl.$^6$ ............... A61K 31/41; A61K 31/415; C07D 257/04
[52] U.S. Cl. ............... 514/381; 514/382; 514/397; 514/307; 548/250; 548/252; 548/253; 548/254; 548/312.1; 546/144
[58] Field of Search ............... 548/250, 252, 253, 254, 548/312.1; 546/144; 514/381, 382, 397, 307

[56] References Cited

U.S. PATENT DOCUMENTS

| | | | |
|---|---|---|---|
| 4,355,040 | 10/1982 | Furukawa et al. | 424/273 |
| 5,128,355 | 7/1992 | Carini et al. | 548/312.1 |
| 5,138,069 | 8/1992 | Carini et al. | 548/312.1 |

FOREIGN PATENT DOCUMENTS

| | | | |
|---|---|---|---|
| 0253310 | 7/1987 | European Pat. Off. | 233/68 |
| 0323841 | 1/1989 | European Pat. Off. | 249/2 |
| 0324377 | 1/1989 | European Pat. Off. | 233/64 |
| 0403158 | 6/1990 | European Pat. Off. | 233/54 |
| 0403159 | 7/1990 | European Pat. Off. | 233/58 |

OTHER PUBLICATIONS

CA 91:206563y The indentification . . . determinations, Inglis et al., p. 271, 1979.
CA 113:23919x Imidazolidine-2,4-dione . . . antagonists, Hemmi et al., p. 663, 1990.

*Primary Examiner*—Mary C. Lee
*Assistant Examiner*—Joseph K. McKane
*Attorney, Agent, or Firm*—Elizabeth M. Anderson

[57] ABSTRACT

This invention relates to novel substituted imidazole and triazole derivatives which antagonize the binding of angiotensin II to its receptors. The compounds are useful in the treatment of hypertension, heart failure, glaucoma, and hyperaldosteronism. Methods of making the compounds, novel intermediates useful in the preparation of the compounds, pharmaceutical compositions containing the compounds, and methods of using them are also covered.

7 Claims, No Drawings

IMIDAZOLE AND 1,2,4-TRIAZOLE DERIVATIVES WITH ANGIOTENSIN II ANTAGONIST PROPERTIES

This is a divisional of U.S. application Ser. No. 07/985,395, filed Dec. 4, 1992, now U.S. Pat. No. 5,322,950, which is a continuation-in-part of U.S. application Ser. No. 07/802,652, filed Dec. 5, 1991, now abandoned.

BACKGROUND OF THE INVENTION

The instant invention relates to novel imidazole and 1,2,4-triazole derivatives which antagonize the binding of angiotensin II (AII) to cellular receptors. This AII antagonist property renders these compounds useful for treatment of angiotensin-related hypertension.

The enzyme renin acts on a blood plasma $\alpha_2$-globulin, angiotensinogen, to produce angiotensin I, which is then converted by angiotensin-converting enzyme to AII. The latter substance is a powerful vasopressor agent which has been implicated as a causative agent for producing high blood pressure in various mammals, such as rats, dogs, and humans. The compounds of this invention inhibit the action of AII at its receptors on target cells and thus prevent the increase in blood pressure produced by this hormone-receptor interaction. By administering a compound of the instant invention to a species of mammal with hypertension due to AII, the blood pressure is reduced. The compounds of the invention are also useful for the treatment of congestive heart failure, hyperaldosteronism and glaucoma.

European Application Number 253,310 (U.S. Pat. No. 5,138,069) discloses imidazoles of the formula

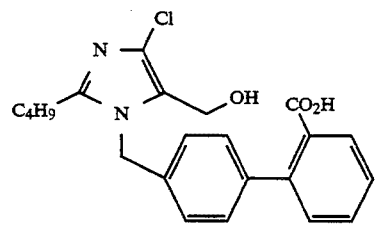

The compounds are disclosed as having utility in treating hypertension and congestive heart failure.

European Application Number 323,841 discloses substituted pyrrole-, pyrazole-, and triazole-containing compounds of the formulas

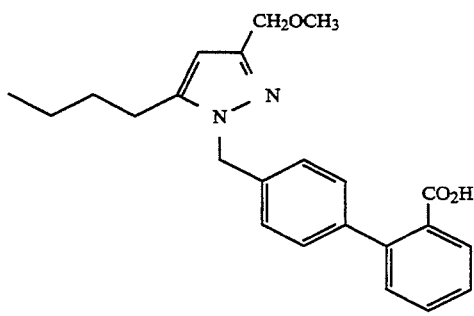

and

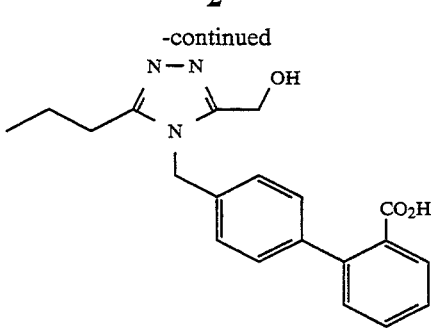

European Application Number 324,37 (U.S. Pat. Nos. 5,128,355 and 5,138,069) discloses a pharmaceutical composition of a diuretic or a nonsteroidal antiinflammatory drug useful for blocking the angiotensin II receptor.

U.S. Pat. No. 4,355,040 discloses imidazole-5-acetic acid derivatives of the formula

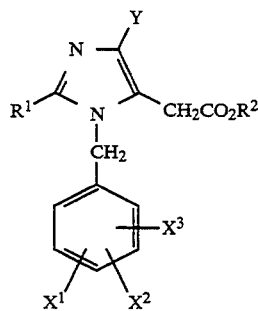

wherein $R^1$ is lower alkyl, cycloalkyl or, phenyl which may be substituted with one to three of halogen, nitro, amino, mono(lower alkyl)amino, di(lower alkyl)amino, lower alkyl, lower alkoxyl, benzyloxyl or/and hydroxyl; $X^1$, $X^2$, and $X^3$ are each hydrogen, halogen, nitro, amino, lower alkyl, lower alkoxyl, benzyloxyl or hydroxyl; Y is halogen and $R^2$ is hydrogen or lower alkyl; provided that $X^1$ is halogen, lower alkyl, lower alkoxyl, benzyloxyl or hydroxyl when $R^1$ is unsubstituted or substituted phenyl only with one halogen, di(-lower alkyl)amino, lower alkyl or lower alkoxyl, and its salts. The compounds are disclosed as having antihypertensive activity.

European Applications Numbers 403158 and 403159 disclose angiotensin II receptor antagonists of formula

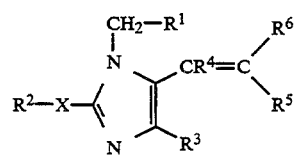

wherein $R^1$ is phenyl, biphenyl, naphthyl, or adamantylmethyl, which are unsubstituted or substituted by one to three substituents selected from Cl, Br, F, I, $C_1$-$C_4$-alkyl nitro $CO_2R^7$ tetrazol-5-yl $C_1$-$C_4$-alkoxy, hydroxy, $SC_1$-$C_4$alkyl, $SO_2NHR^7$, $SO_3H$, $CONR^7R^7$, CN, $SO_2C_1$-$C_4$alkyl or $C_nF_{2n1}$, wherein n is 1 to 3;

$R^2$ is $C_2$-$C_{10}$alkyl, $C_3$-$C_{10}$alkenyl, $C_3$-$C_{10}$alkynyl, $C_3$-$C_6$cycloalkyl, , or $(CH_2)_{0-3}$phenyl unsubstituted or substituted by one to three substituents selected from $C_1$-$C_4$alkyl, nitro, Cl, Br, F, I, hydroxy, $C_1$-$C_4$alkoxy, or $NR^7R^7$;

X is a single bond, S, or O:

$R^3$ is hydrogen, Cl, Br, F, I, CHO, hydroxymethyl, $COOR^7$, $CONR^7R^7$, $NO_2$, or $C_nF_{2n1}$, wherein n is 1 to 3;

$R^4$ and $R^5$ are independently hydrogen, $C_1$-$C_5$alkyl, phenyl—Y—, naphthyl—Y—, or biphenyl—Y—, wherein the aryl groups are unsubstituted or substituted by one to three substituents selected from Cl, Br, F, I, $C_1$-$C_4$alkoxy, hydroxy, $CO_2R^7$, CN, $NO_2$, tetrazol-5-yl, $SO_3H$, $CF_3$, $CONR^7R^7$, $SO_2NHR^7$, $C_1$-$C_4$-alkyl, or $NR^7R^7$, or by methylenedioxy, phenoxy, or phenyl, except that $R^4$ and $R^5$ are not both selected from hydrogen or $C_1$-$C_6$alkyl;

Y is a single bond, O, S, or $C_1$-$C_6$alkyl which is straight or branched or optionally substituted by phenyl or benzyl, wherein each of the aryl groups is unsubstituted or substituted by halo, $NO_2$, $CF_3$, $C_1$-$C_4$alkyl, $C_1$-$C_4$alkoxy, CN, or $CO_2R^7$;

$R^6$ is —Z—$COOR^6$ or —Z—$CONR^7R^7$;

Z is a single bond, vinyl, $CH_2$—O—$CH_2$—, methylene optionally substituted by $C_1$-$C_4$alkyl, one or two benzyl groups, thienylmethyl, or furylmethyl, or —C(O)NHCHR$^9$—, wherein $R^9$ is H, $C_1$-$C_4$alkyl, phenyl, benzyl, thienylmethyl, or furylmethyl;

each $R^7$ independently is hydrogen, $C_1$-$C_4$alkyl, or $(CH_2)_m$phenyl, wherein m is 0 to 4; and $R^6$ is hydrogen, $C_1$-$C_6$alkyl, or 2-di($C_1$-$C_4$alkyl)amino-2-oxoethyl; or $R^5$ and $R^6$ are both hydrogen, $R^4$ is and —Z—$COOR^8$ and Z is other than a single bond; or a pharmaceutically acceptable salt thereof.

Copending U.S. application Ser. No. 07/757021 covers novel anilide derivatives which antagonize the binding of angiotensin II to its receptors. The compounds are those of formula

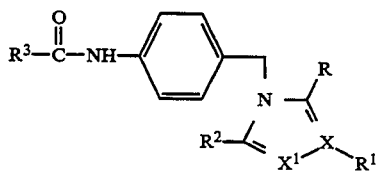

SUMMARY

The instant invention concerns a compound of formula

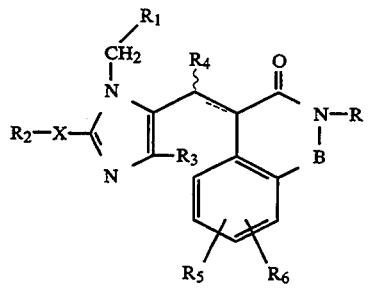

I or the pharmaceutically acceptable acid addition or basic salts thereof wherein X, B, R, $R_1$, $R_2$, $R_3$, $R_4$, $R_5$, and $R_6$ are as defined below.

Angiotensin II mediates a variety of responses in various tissues, including contraction of vascular smooth muscle, excretions of salt and water from kidney, release of prolactin from pituitary, stimulation of aldosterone secretion from adrenal gland, and possible regulation of cell growth in both cardiac and vascular tissue. As antagonists of angiotensin II, the compounds of Formula I are useful in controlling hypertension, hyperaldosteronism, and congestive heart failure in mammals. Additionally, antihypertensive agents as a class have been shown to be useful in lowering intraocular pressure. Thus, the compounds of Formula I are also useful in controlling glaucoma..

The invention also includes a pharmaceutical composition comprising an antihypertensive effective amount of a compound of Formula I above in admixture with a pharmaceutically acceptable carrier or excipient and a method for treating hypertension in a mammal suffering therefrom which comprises administering to said mammal the above pharmaceutical composition in unit dosage form.

Further, the invention includes a pharmaceutical composition comprising an amount of a compound of Formula I above effective for treating hyperaldosteronism in admixture with a pharmaceutically acceptable carrier or excipient, and a method for treating hyperaldosteronism in a mammal suffering therefrom comprising administering to said patient the above pharmaceutical composition in unit dosage form.

Also, the invention includes a pharmaceutical composition comprising an amount effective for treating congestive heart failure of a compound of Formula I above in admixture with a pharmaceutically acceptable carrier or excipient and a method of treating congestive heart failure in a patient suffering therefrom comprising administering to said patient the above pharmaceutical composition in unit dosage form.

Also the invention includes a pharmaceutical composition comprising an amount of a compound of Formula I above effective for treating glaucoma in admixture with a pharmaceutically acceptable carrier or excipient; and a method of treating glaucoma in a patient suffering therefrom comprising administering to said patient the above pharmaceutical composition in unit dosage form.

The instant invention further includes methods for making compounds of Formula I.

DETAILED DESCRIPTION

The compounds of the present invention are represented by the formula

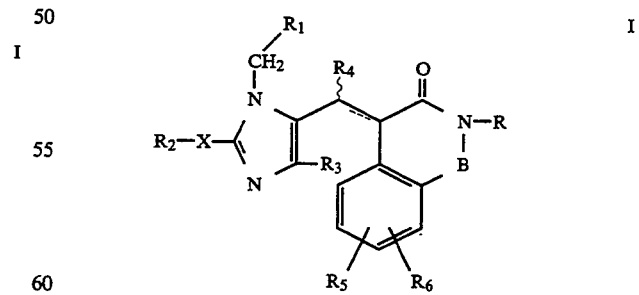

I or a pharmaceutically acceptable salt thereof wherein
$R_1$ is adamantylmethyl,
phenyl,
biphenyl, or
naphthyl, each of which is unsubstituted or substituted by one to three substituents selected from Cl, Br,
F,
I,
alkyl of from one to four carbon atoms,
nitro,
tetrazol-5-yl,
alkoxy of from one to four carbon atoms,
hydroxy,
$SO_3H$,
$SO_2$alkyl of from one to four carbon atoms,
CN,
$C_nF_{2n+1}$ wherein n is an integer of from 1 to 3,
$CO_2R_4$,
$SO_2NHR_4$,
$NHSO_2R_4$,
$NHSO_2C_nF_{2n+1}$,
$CON(R_4)_2$ wherein $R_4$ is hydrogen or lower alkyl;

X is a single bond, S, or O;

$R_2$ is alkyl of from two to ten carbon atoms, alkenyl of from two to ten carbon atoms, alkynyl of from three to ten carbon atoms, cycloalkyl of from three to six carbon atoms, $(CH_2)_m$phenyl wherein m is an integer of from zero to eight and phenyl is unsubstituted or substituted by one to three substituents selected from
alkyl of from one to four carbon atoms,
nitro,
Cl,
Br,
F,
I,
hydroxy,
alkoxy of from one to four carbon atoms, or
$NR_4R_4$ wherein $R_4$ is as defined above;

$R_3$ is hydrogen,
Cl,
Br,
F,
I,
CHO,
hydroxymethyl,
alkyl,
aryl,
heteroaryl,
$CO_2R_4$,
$CONR_4R_4$,
$NO_2$, or
$C_nF_{2n+1}$ wherein n is as defined above;

$R_4$ is hydrogen or alkyl of from one to five carbon atoms,

R is hydrogen or alkyl of from one to five carbon atoms which alkyl is unsubstituted or substituted with
CN,
$CO_2R_4$,
tetrazol-5-yl,
$CONHR_4$,
$CONH(CH_2)_nCO_2R_4$
phenyl unsubstituted or substituted by one to three substituents selected from
alkyl of from one to four carbon atoms,
nitro,
Cl,
F,
I,
hydroxy,
alkoxy of from one to four carbon atoms, or
$NR_4R_4$ wherein $R_4$ is as defined above;

Additionally, R is
$OR_4$,
$O(CH_2)_nCO_2R_4$.

$R_5$ and $R_6$ are each independently
hydrogen,
halogen,
alkyl of from one to five carbon atoms,
alkyloxy of from one to five carbon atoms,
$NO_2$,
$NHCOR_4$,
$NHSO_2R_4$,
$(CH_2)_nCO_2R_7$ wherein n and $R_4$ are as defined above; and B is a bond, or CO; and
the ---- indicates a double or single bond.

More preferred compounds of the invention are those of Formula I wherein
$R_1$ is phenyl
biphenyl, or
naphthyl, each of which is unsubstituted or substituted by one to three substituents selected from
Cl,
F,
alkyl of from one to four carbon atoms,
nitro,
tetrazol-5-yl,
alkoxy of from one to four carbon atoms,
hydroxy,
$SO_3H$,
CN,
$C_nF_{2n+1}$ wherein n is an integer of from 1 to 3,
$CO_2R_4$,
$SO_2NHR_4$,
$NHSO_2R_4$,
$CONR_4R_4$ wherein $R_4$ is hydrogen or lower alkyl;

X is a single bond or S;

$R_2$ is alkyl of from two to eight carbon atoms, or cycloalkyl of from three to six carbon atoms, $R_3$ is hydrogen,
Cl,
F,
I,
CHO,
hydroxymethyl,
alkyl,
aryl,
pyrrole,
$CO_2R_4$,
$CONR_4R_4$,
$NO_2$, or
$C_nF_{2n+1}$ wherein n is as defined above;

$R_4$ is hydrogen or alkyl of from one to four carbon atoms,

R is hydrogen or alkyl of from one to four carbon atoms unsubstituted or substituted with
$CO_2R_4$,
tetrazol-5-yl,
$CONHR_4$ wherein $R_4$ is as defined above;

$R_5$ and $R_6$ are each independently
hydrogen,
alkyl of from one to four carbon atoms,
alkyloxy of from one to four carbon atoms,
$NO_2$,
$NHCOR_4$,
$NHSO_2R_4$, $(CH_2)_nCO_2R_4$ wherein n, $R_4$, is as defined above; and B is a bond, or CO.

The ═ indicates a double bond

Still more preferred compounds of the invention are those of Formula I wherein $R_1$ is phenyl substituted by one to three substituents selected from
Cl,
F,
trifluoromethyl,
nitro,
methyl,
methoxy,
hydroxy,
sulfonamido,
carboxy,
carbo$C_1$–$C_4$alkoxy,
carbamoyl,
CN, or
tetrazol-5-yl;

X is a single bond;

$R_2$ is alkyl of from two to eight carbon atoms;

$R_3$ is hydrogen, $R_4$ is hydrogen,

R is $CH_2CO_2R_4$ wherein $R_4$ is hydrogen or lower alkyl;

$R_5$ is alkyl of from one to four carbon atoms;

$R_6$ is hydrogen; and

B is a bond.

The ═ indicates a double bond.

Most especially preferred compounds of the invention are:

Ethyl 4-[[2-butyl-5-[(1,2-dihydro-2-oxo-3H-indol-3-ylidene)methyl]-1H-imidazol-1-yl]methyl]benzoate;

Methyl 4-[[2-butyl-5-[(1,2-dihydro-2-oxo-3H-indol-3-ylidene)methyl]-1H-imidazol-1-yl]methyl]-3-chlorobenzoate;

Methyl 4-[[2-butyl-5-[(1,2-dihydro-5-methyl-2-oxo-3H-indol-3-ylidene)methyl]-1H-imidazol-1-yl]methyl]benzoate;

Ethyl 4-[[2-butyl-4-chloro-5-[(1,2-dihydro-6-methyl-2-oxo-3H-indol-3-ylidene)methyl]-1H-imidazol-1-yl]methyl]benzoate;

Methyl 4-[[2-propyl-5-[(1,2-dihydro-1-methyl-2-oxo-3H-indol-3-ylidene)methyl]-1H-imidazol-1-yl]methyl]benzoate;

Methyl 4-[[2-butyl-5-[(1,2-dihydro-4-methyl-2-oxo-3H-indol-3-ylidene)methyl]-1H-imidazol-1-yl]methyl]benzoate;

Methyl 4-[[2-butyl-5-[(1,2-dihydro-7-methyl-2-oxo-3H-indol-3-ylidene)methyl]-1H-imidazol-1-yl]methyl]benzoate;

Methyl 4-[[2-butyl-5-[(5-chloro-1,2-dihydro-2-oxo-3H-indol-3-ylidene)methyl]-1H-imidazol-1yl]methyl]benzoate;

Methyl 4-[[2-butyl-5-[(1,2-dihydro-7-methoxy-2-oxo-3H-indol-3-ylidene)methyl]-1H-imidazol-1-yl]methyl]benzoate;

Ethyl 3-[[2-butyl-1-[[4-(methoxycarbonyl)phenyl]methyl]-1H -imidazol-5-yl]methylene]-2,3-dihydro-2-oxo-1H-indole-5-carboxylate;

Ethyl 4-[[2-butyl-4-chloro-5-[(1,2-dihydro-2-oxo-3H-indol-3-ylidene)methyl]-1H-imidazol-1-yl]methyl]benzoate;

Ethyl 3-[[2-butyl-1-[[(4-methoxycarbonyl)phenyl]methyl]-1H-imidazol-5-yl]methylene]-2,3-dihydro-2-oxo-1H-indole-1-acetate;

(E)-4-[[2-butyl-4-chloro-5-[(1,2-dihydro-2-oxo-3H-indol-3-ylidene)methyl]-1H-imidazol-1-yl]methyl]benzoic acid;

4-[[2-butyl-5-[(1,2-dihydro-2-oxo-3H-indol-3-ylidene)methyl]-1H-imidazol-1-yl]methyl]benzoic acid;

4-[[2-butyl-5-[(1,2-dihydro-7-methoxy -2-oxo-3H-indol-3-ylidene)methyl]-1H-imidazol-1-yl]methyl]benzoic acid;

3-[[2-butyl-1-[(4-carboxyphenyl)methyl]-1H-imidazol-5-yl]methylene]-2,3-dihydro-2-oxo-1H-indole-1-acetic acid;

3-[[2-butyl-1-[(4-carboxyphenyl)methyl]-1H-imidazol-5-yl]methylene]-2,3-dihydro-2-oxo-1H-indole-5-carboxylic acid;

4-[[2-butyl-5-[(1,2-dihydro-5-methyl-2-oxo-3H-indol-3-ylidene)methyl]-1H-imidazol-1-yl]methyl]benzoic acid;

3-[[2-butyl-1-[[2'-carboxy-[1,1'-biphenyl]-4-yl]methyl]-1H-imidazol-5-yl]methylene]-2,3-dihydro-2-oxo-1H-indole-1-acetic acid;

4-[[2 -butyl-5-[(1,2-dihydro-1-methyl-2-oxo-3H-indol-3-ylidene)methyl]-1H-imidazol-1-yl]methyl]benzoic acid;

4-[[5-[[1-(aminocarbonyl)-1,2-dihydro-2-oxo-3H-indol-3-ylidene]methyl]-2-butyl-1H-imidazol-1-yl]methyl]benzoic acid;

Methyl 4-[[(2-propyl-5-[1,2-dihydro-1-(methylaminocarbonyl)-2-oxo-3H-indol-3-ylidene]methyl]-1H-imidazol-1-yl]methyl benzoate;

Methyl 4-[[2-butyl-5-[1,2-dihydro-1-hydroxy-2-oxo-3H-indol-3-ylidene)methyl]-1H-imidazol-1-yl]methyl]benzoate;

Ethyl (Z)-(±)-2,3-dihydro-3-[[3-[[4-(methoxycarbonyl)phenyl]methyl]-2-propyl-3H-imidazol-4-yl]methylene]-4-methyl-2-oxo-α-propyl-1H-indole-1-acetate;

3-[[2-butyl-3-[[4-(1H-tetrazol-5-yl)phenyl]methyl]-3 H-imidazol-4-yl]methylene]-2,3-dihydro-2-oxo-1H-indole-1-acetic acid;

Methyl (Z)-2,3-dihydro-3-[[3-[[4-(methoxycarbonyl)-phenyl]methyl]-2-propyl-3H-imidazol-4-yl]methylene]-4-methyl-2-oxo-1H-indole-1-acetate;

4-[[2-butyl-5-[(1-butyl-1,2-dihydro-2-oxo-3H-indol-3-ylidenyl)methyl]-1H-imidazol-1-yl]methyl]-3 chlorobenzoic acid;

4-[[2-butyl-5-[(1,2-dihydro-7-methyl-2-oxo-3H-indol-3-ylidenyl)methyl]-1H-imidazol-1-yl]methyl]benzoic acid;

4-[[5-[(1,2-dihydro-2-oxo-1-propyl-3H-indol-3-ylidenyl)methyl]-2-propyl-1H-imidazol-1-yl]methyl]benzoic acid;

(E)-4-[[5-[(1,2-dihydro-2-oxo-3H-indol-3-ylidenyl)methyl]-2-propyl-4-(1H-pyrrol-1-yl)-1H-imidazol-1-yl]methyl]benzoic acid;

Ethyl (Z)-3-[[2-butyl-3-[[4-(methoxycarbonyl)phenyl]methyl]-3H-imidazol-4-yl]methylene]-2,3-dihydro-7-methoxy-2-oxo-1H-indole-1-acetate;

Methyl 4-[[5-[(1,2-dihydro-1-methyl-2-oxo-3H-indol-3-ylidenyl)methyl]-2-propyl-1H-imidazol-1-yl]methyl]benzoate;

Methyl 2,3-dihydro-3-[[3-[[4-(methoxycarbonyl)-phenyl]methyl]-2-propyl-3H-imidazol-4-yl]methylene]-2-oxo-1H-indole-7-acetate;

(E)-3-[[3-[(4-carboxyphenyl)methyl]-2-propyl-3H-imidazol-4-yl]methylene]-2,3-dihydro-2-oxo-1H-indole-1-acetic acid;

Benzoic acid, 4-[[2-butyl-5-[[1-[(4-chlorophenyl)methyl]-2,3-dihydro-2-oxo-1H-indol-3-ylidene]methyl]-1H-imidazol-1-yl]methyl]-, (E)-;

1H-Indole-1-propanoic acid, 3-[[2-butyl-1-[(4-carboxyphenyl)methyl]-1H-imidazol-5-yl]methylene]-2,3-dihydro-2-oxo -, (E)-;

Benzoic acid, 4-[[2-butyl-5-[[2,3-dihydro-2-oxo-1-[(1H-tetrazol-5-yl)methyl]-1H-indol-3-ylidene]methyl]-1H-imidazol-1-yl]methyl]-, methyl ester, (E)-;

1H-Indole-1-propanoic acid, 3-[[2-butyl-1-[[4-methoxycarbonyl)phenyl]methyl]-1H-imidazol-5-yl]methylene]-2,3-dihydro-2-oxo-, ethyl ester, (E)-;

Benzoic acid, 4-[[2-butyl-5-[[1-(cyanomethyl)-2,3-dihydro-2-oxo-1H-indol-3-ylidene]methyl]-1H-imidazol-1-yl]methyl]-, methyl ester, (E);

Benzoic acid, 4-[[2-butyl-5-[[1-[2-(dimethylamino)ethyl]-2,3-dihydro-2-oxo-1H-indol-3-ylidene]methyl]-1H-imidazol-1-yl]methyl]-, methyl ester, (E)-;

1H-Indole-1-acetic acid, 3-[[2-butyl-1-[[4-(1H-tetrazol-5-yl) phenyl]methyl]-1H-imidazol-5-yl]methylene]-2,3-dihydro-2-oxo-, methyl ester;

Benzoic acid, 4-[[5-[(2,3-dihydro-1-methyl-2-oxo-1H-indol-3-ylidene)methyl]-2-propyl-4-(1H-pyrrol-1-yl)-1H-imidazol-1-yl]methyl]-, methyl ester, (E)-;

Benzoic acid, 4-[[2-butyl-5-[(1-butyl-2,3-dihydro-2-oxo-1H-indol-3-ylidene)methyl]-1H-imidazol-1-yl]methyl]-, methyl ester;

1H-Indole-1-acetic acid, 2,3-dihydro-3-[[1-[[4-(methoxycarbonyl) phenyl]methyl]-2-propyl-4-(1H-pyrrol-1-yl)-1H-imidazol-5-yl]methylene]-2-oxo -, methyl ester, (E);

Benzoic acid, 4-[[5-[[2,3-dihydro-1-(1-methylethyl)-2-oxo-1H-indol-3-ylidene]methyl]-2-propyl-1H-imidazol-1-yl]methyl]-, methyl ester, (Z)-;

Benzoic acid, 4-[[5-[(1-butyl-2,3-dihydro-2-oxo-1H-indol-3-ylidene)methyl]-2-propyl-4-(1H-pyrrol-1-yl)-1H-imidazol-1-yl]methyl]-, methyl ester, (E)-;

Benzoic acid, 4-[[2-butyl-5-[[2,3-dihydro-1-(2-methoxy-2-oxoethoxy)-2-oxo-1H-indol-3-ylidene]methyl]-1H-imidazol-1-yl]methyl]-, methyl ester;

1H-Indole-1-acetic acid, 3-[[2-butyl-1-[[4-(1H-tetrazol-5-yl) phenyl]methyl]-1H-imidazol-5-yl]methylene]-2,3-dihydro-2-oxo-, ethyl ester;

Benzoic acid, 4-[[5-[(2,3-dihydro-2-oxo-1H-indol-3-ylidene)methyl]-2-ethyl-4-methyl-1H-imidazol-1-yl]methyl]-(E)-;

2 (1H)-Isoquinolineacetic acid, 3,4-dihydro-4-[[1-[[4-(methoxycarbonyl)phenyl]methyl]-2-propyl-1H-imidazol-5-yl]methylene]-1,3-dioxo-, methyl ester, (Z)-;

Benzoic acid, 4-[[2-butyl-5-[(2,3-dihydro-2-oxo-1H-indol-3-yl)methyl]-1H-imidazol-1-yl]methyl]-, methyl ester; and their pharmaceutically acceptable salts.

Both the E and Z isomers are within the scope of the invention.

The E-isomers (trans stereochemistry of the carbonyl and imidazole groups) are generally more active and thus, are preferred over the Z-isomers.

The compounds of the instant invention include solvates, hydroares, and pharmaceutically acceptable acid addition and/or base salts of the compounds of Formula I above.

The term pharmaceutically acceptable acid addition salt is intended to mean a relatively nontoxic acid addition salt either from inorganic or organic acids such as, for example, hydrochloric, hydrobromic, hydroiodic, sulfuric, phosphoric, acetic, citric, oxalic, malonic, salicylic, malic, benzoic, gluconic, fumaric, succinic, ascorbic, maleic, tartaric, methanesulfonic, and the like. The salts are prepared, when applicable, by contacting the free base form with a sufficient amount of the desired acid to produce a salt in the conventional manner. The free base forms may be regenerated by treating the salt form with a base.

When the compounds are in the free carboxylic acid form the pharmaceutically suitable salts also include both the metallic (inorganic) salts and organic salts; a list of which is given in Remington's Pharmaceutical Sciences, 17th Edition, 1985:1418. It is well known to one skilled in the art that an appropriate salt form is chosen based on physical and chemical stability, flowability, hydroscopicity, and solubility. Preferred salts of this invention for the reasons cited above include potassium, sodium, calcium, and ammonium salts.

The compounds of the present invention possess one or more chiral centers and each center may exist in the R(D) or S(L) configuration. The present invention includes all enantiomeric and epimeric forms as well as the appropriate mixtures thereof.

The instant invention includes a process for the preparation of compounds of Formula I.

The term lower alkyl refers to straight or branched chain alkyl radicals containing from one to ten carbon atoms except where specifically stated including but not limited to methyl, ethyl, n-propyl, isopropyl, n-butyl, iso-butyl, sec-butyl, 2-methylhexyl, n-pentyl, 1-methylbutyl, 2,2-dimethylbutyl, 2-methyl-pentyl, 2,2-dimethylpropyl, n-hexyl, and the like.

The term halogen refers to bromine, chlorine, iodine, and fluorine.

The term cycloalkyl refers to cyclic alkyl groups containing three to six carbon atoms.

The term aryl refers to phenyl and 1- or 2-naphthyl, unsubstituted or substituted by $CH_3$, $OCH_3$, OH, Br, Cl, F, $NO_2$, $NH_2$, $N(CH_3)_2$, $SCH_3$, SH.

Heteroaryl refers to 5- or 6-membered rings or 8-, 9-, or 10-membered twin rings containing one or more heteroatoms selected from N, O, S, and includes but is not limited to: pyrrole, imidazole, thiophene, furane, pyridine, thiazole, indole, morpholine, isoquinoline.

Scheme I below illustrates one of the preparation of known starting materials (J Med Chem 1991; 34:1514–7, U.S. Pat. No. 4,207,324, and U.S. Pat. No. 4,355,040), the disclosure of which is hereby incorporated by reference.

Scheme II outlines another procedure useful for compounds wherein $R_3$ is a group other than halo.

The 1—$R^1$CH-group is incorporated onto the 2-$R_2$X-imidazole by known procedures, for example, by reaction with an $R^1$—$CH_2$ halide, mesylate or acetate, such as 2-chlorobenzyl bromide, in a suitable solvent, such as dimethylformamide (DMF), in the presence of a suitable acid acceptor, such as sodium alkylate, potassium or sodium carbonate, or a metal hydride, preferably sodium hydride, at a reaction temperature of 25°–100° C., preferably 50° C. The resulting 1—$R^1CH_2$—2—$R^2$ imidazole is hydroxymethylated in the 5-position, for example, by reacting with formaldehyde in the presence of sodium acetate in acetic acid to provide the 1—$R^1$—$CH_2$—2—$R^2$X—5 hydroxymethylimidazole intermediates.

The hydroxymethyl group of the hereinbefore prepared intermediate is oxidized to an aldehyde by treatment with a suitable reagent, such as anhydrous chromic acid silica gel in tetrahydrofuran or, preferably, with activated manganese dioxide, in a suitable solvent such as benzene, or toluene, or preferably methylene chloride, at a temperature of 25°–140° C., preferably at 25° C.

Alternatively the 1—$R^1CH_2$—2—$R_2$—5 hydroxymethylimidazole intermediates are prepared by reacting an amidine, $R_2$—C(=NH)—$NH_2$ such as valeramidine, with dihydroxyacetone in liquid ammonia under pressure to give 2—$R^2$—5-hydroxymethylimidazole (Irabach J L, Jacquier R, Lacombe J M, Mawry G, *Bull Soc Chim Fr* 1971:1052). This intermediate is reacted with acetic anhydride to give 1-acetyl-5-acetoxymethyl-2—$R_2$-imidazole. The diacetate intermediate is N alkylated, for example, using 2-chlorobenzyl triflate and the resulting 1—$R^1CH_2$-2—$R_2$—5-acetoxymethylimidazole is treated with aqueous base, such as 10% sodium hydroxide solution to give the 1—$R^1CH_2$—2—$R_2$—5-hydroxymethylimidazole intermediate which can be oxidized as before to the aldehyde 2b (see Scheme Scheme IV below illustrates the synthesis of the compounds of structure 1. Compounds of the structure 2 are reacted with the requisite oxo-methylene substrate, for example, 6 under acid catalyzed (Method A) or base catalyzed (Method B) condition to afford 3. Compounds 3 are treated with base, such as KOH, LiOH, or NaOH in aqueous alcohol or diglyme, to yield the desired carboxylic acid 5. Alternatively, compounds 2 are treated with base to give acids 4 which are then reacted with 6 to provide compounds 5. Method A uses acid such as, but not limited to, acetic acid, propionic acid, etc., containing p-toluene sulfonic acid, β-alanine, anhydrous NaAc, trifluoro acetic anhydride, acetic anhydride, etc. Method B uses solvents such as, but not limited to, ethanol, toluene, xylene-containing piperidine, $Et_3N$, sodium methoxide, etc.

The (E)- and (Z)-isomers are separated either at the ester stage (compound 3) by column chromatography or at the acid stage (compound 5) by crystallization.

For compounds where the substituted oxindoles are not easily accessible are obtained from compound 3 via alkylation as shown in Scheme V. Compound 3 is treated with the requisite alkyl halide in the presence of a base (for example, $Cs_2CO_3$) in DMF to give compound of structure 7. This can be treated with NaOH in aqueous alcohol to give the desired acid 8.

The 1—$R^1CH$—2—$R_2X$-imidazol-5-carboxaldehydes are reacted with an appropriate phosphonate (Scheme VI). The phosphonates are prepared, for example, from trialkyl phosphonoacetates by alkylation with an appropriate halide, mesylate or acetate in the presence of a suitable base, such as sodium hydride, DBU in a suitable solvent, preferably glyme at a reaction temperature of 25°–100° C., preferably at 55° C. The reaction of the imidazol 5 carboxaldehydes with the phosphonates is performed in the presence of a suitable base, such as a metal alkoxide, lithium hydride or, preferably, sodium hydride, in a suitable solvent, such as ethanol, methanol, ether, dioxane, tetrahydrofuran or, preferably glyme, at a reaction temperature of 10°–50° C., preferably, at 25° C., to provide a variable mixture of trans and cis, e.g., (E) and (Z). The trans and cis structures of the acids are readily determined by NMR by the NOE protocol, as well as by the biological activities since, generally, the trans (E)-isomers are the more potent isomers.

Compounds of structure (I) are also prepared as follows. The 1—$R^1$—($CH_2$)—2—$R^2X$-imidazol-5-carboxaldehydes are treated with the lithium derivative of an active methylene substrate, such as 6. These lithio derivatives are prepared from the reaction of lithium diisopropylamide in as suitable solvent, preferably tetrahydrofuran, with an acid ester, such as ROOC—$CH_2$—Y-phenyl, to generate the α-lithio derivatives at −78° to −10° C., preferably at −78° C., which are then treated with the imidazolcarboxaldehyde. The intermediates β-hydroxy group of the imidazole ester is converted to a mesylate or an acetate and the mesylate, or preferably the acetate, is heated in a suitable solvent, such as toluene, with one to two equivalents of 1,8-diazobicyclo[5.4.0]undec-7-ene, at 50°–110° C., preferably at 80° C., to afford compounds of structure (1). The (E)-isomer is the predominate olefinic isomer. The acids are prepared from the esters by the method described above.

The starting materials 6 are prepared by known procedures.

Another alternative procedure to prepare compounds of structure I is outlined in Scheme VII. The 4-chloro-5-formyl imidazole is reduced to give the 5-formyl imidazole (10) which reacted with oxindole 9 (or 6) in the presence of a base as before to give the condensation product 11. This is converted to the N-protected (for example, Boc, trityl, acetyl, POM, etc.) imidazole derivative 12 by reacting with BOC-chloride in the presence of a base in DMF. Compound 12 is converted to the target compound 3 by triflic anhydride/requisite benzyl alcohol method.

Scheme VIII outlines the synthesis of compound 2 wherein the ester functionality is replaced with a tetrazole moiety. p-Tolunitrile is converted to the tetrazole compound via standard reaction condition using $NaN_3/NH_4Cl$/DMF. The tetrazole is protected with a trityl group by the reaction of tritylchloride in the presence of $Et_3N$ in DMF. This is converted to the corresponding bromide which is then condensed with the imidazole 1 as before to give the desired chloroaldehyde. This is converted to the corresponding hydrogen compound 13 by catalytic reduction. This is reacted with the oxindole to give compound 14 as described before. This is converted to the free tetrazole compound 15 by treatment with MeOH. Alternatively, compound 14 is alkylated to introduce a substitution at the nitrogen by treatment with the desired alkyl halide in presence of a base. Subsequent treatment with MeOH gives compound 16. In addition, compound 16, wherein R' is a $CO_2Me$ (or $CO_2Et$) group, is saponified to give the desired acid 17.

One example of the synthesis of the starting material where $R_3$ is a heterocycle is shown in Scheme IX. The requisite imidate-HCl is reacted with ethyl amino cyano acetate (Shaw et al, *Chemistry and Industry* 1981:542) in the presence of KOAc in methanol to give the 4-amino imidazole-5-carboxylate derivative. This is treated with 2,5-dimethoxy tetrahydrofuran in AcOH under refluxing condition to give the desired pyrrole derivative. The ester moiety is converted to the carboxaldehyde 18 in two steps which is used for N-benzylation as before.

Scheme X outlines a general procedure to prepare compounds of Formula I where the double bond is reduced.

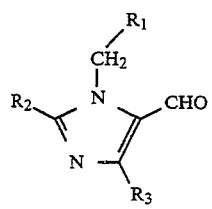
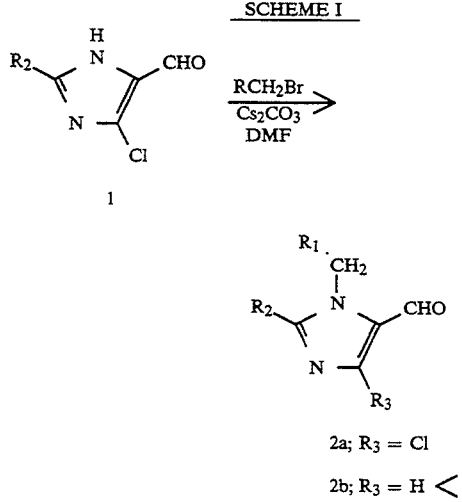
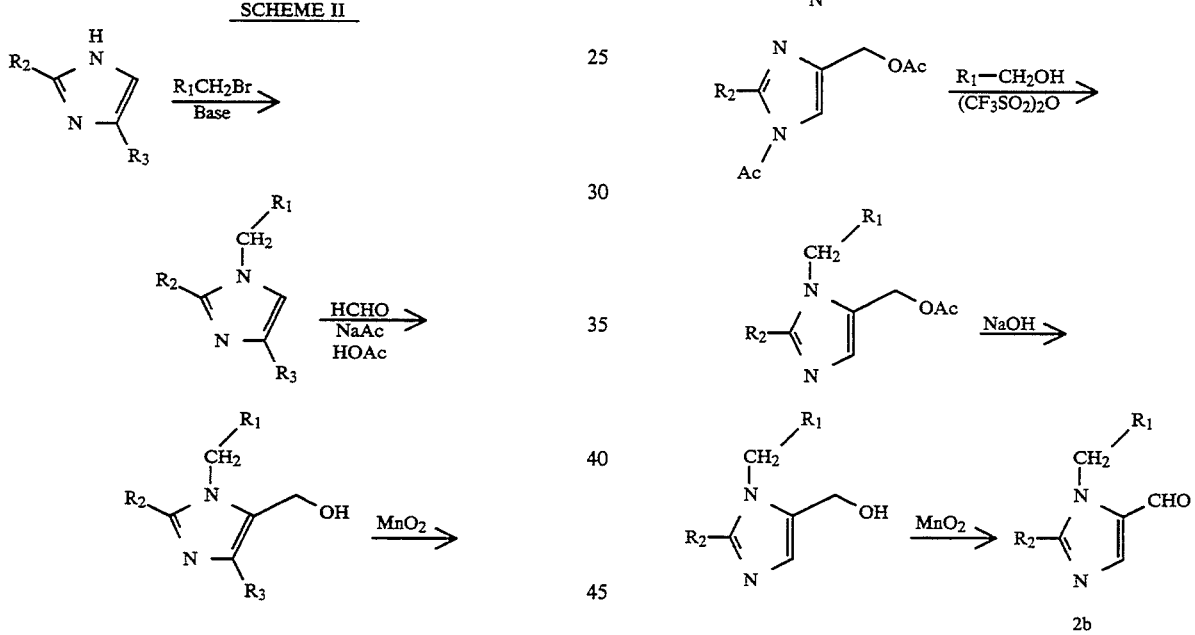
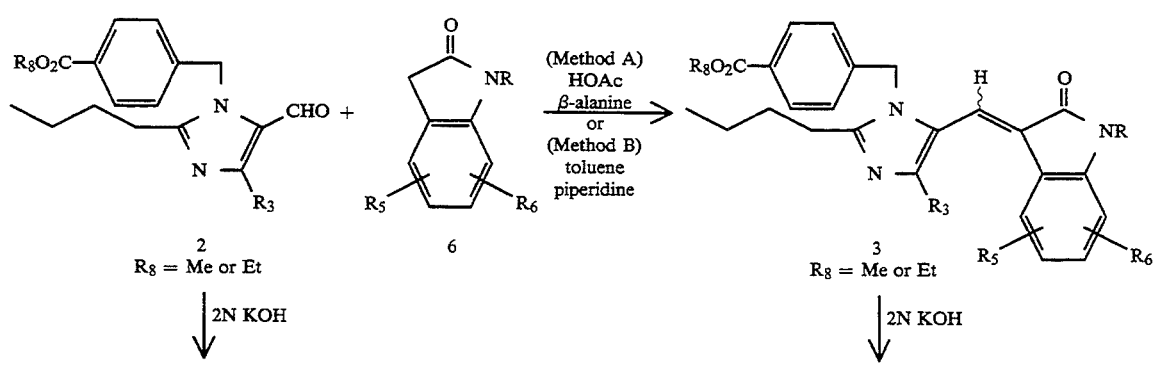

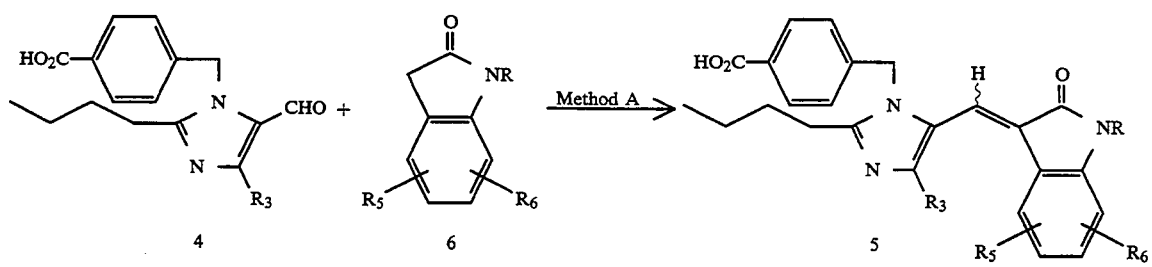
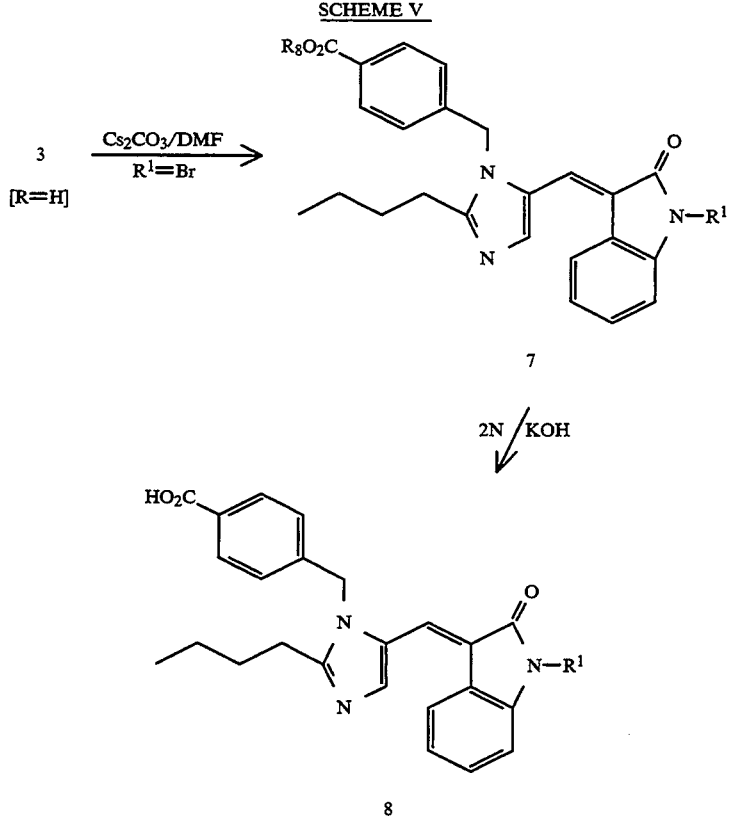
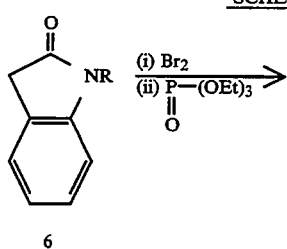
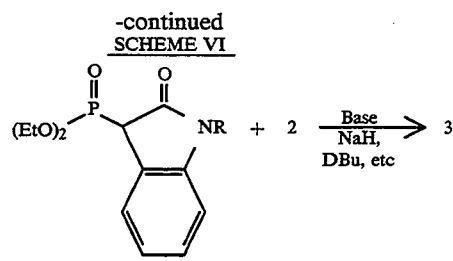
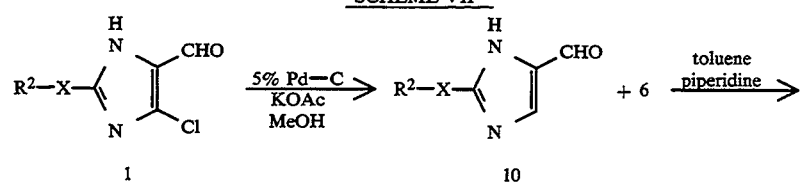

SCHEME VII
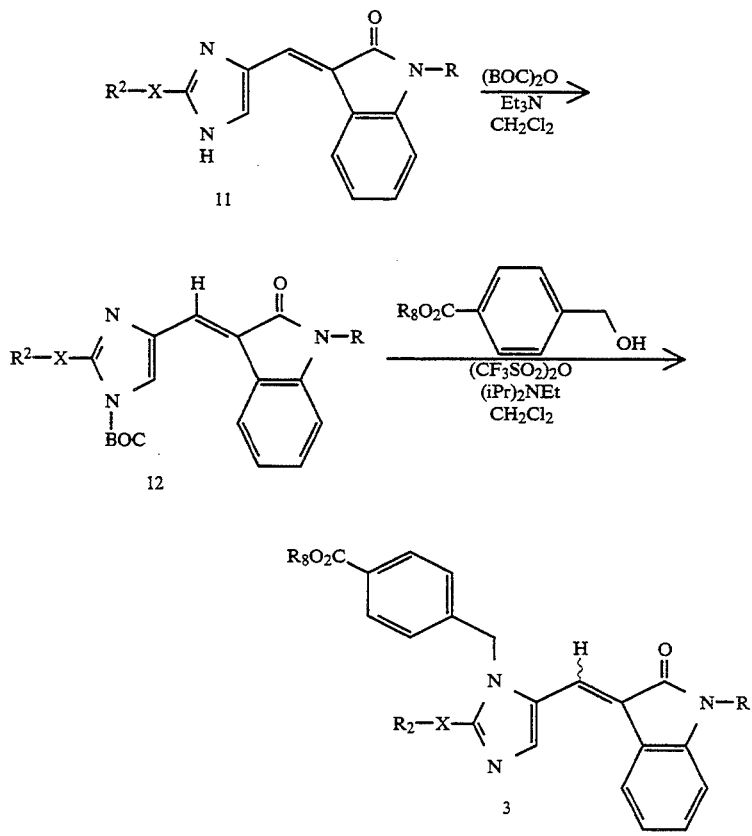
SCHEME VIII
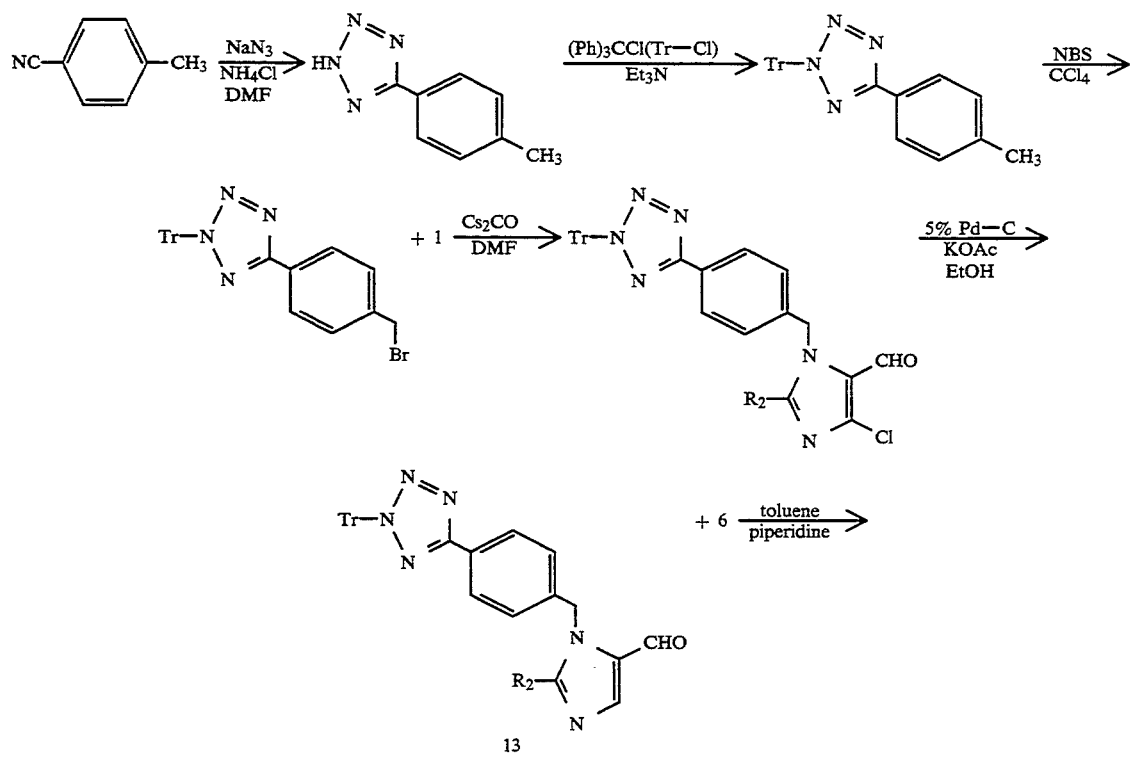

-continued
SCHEME VIII
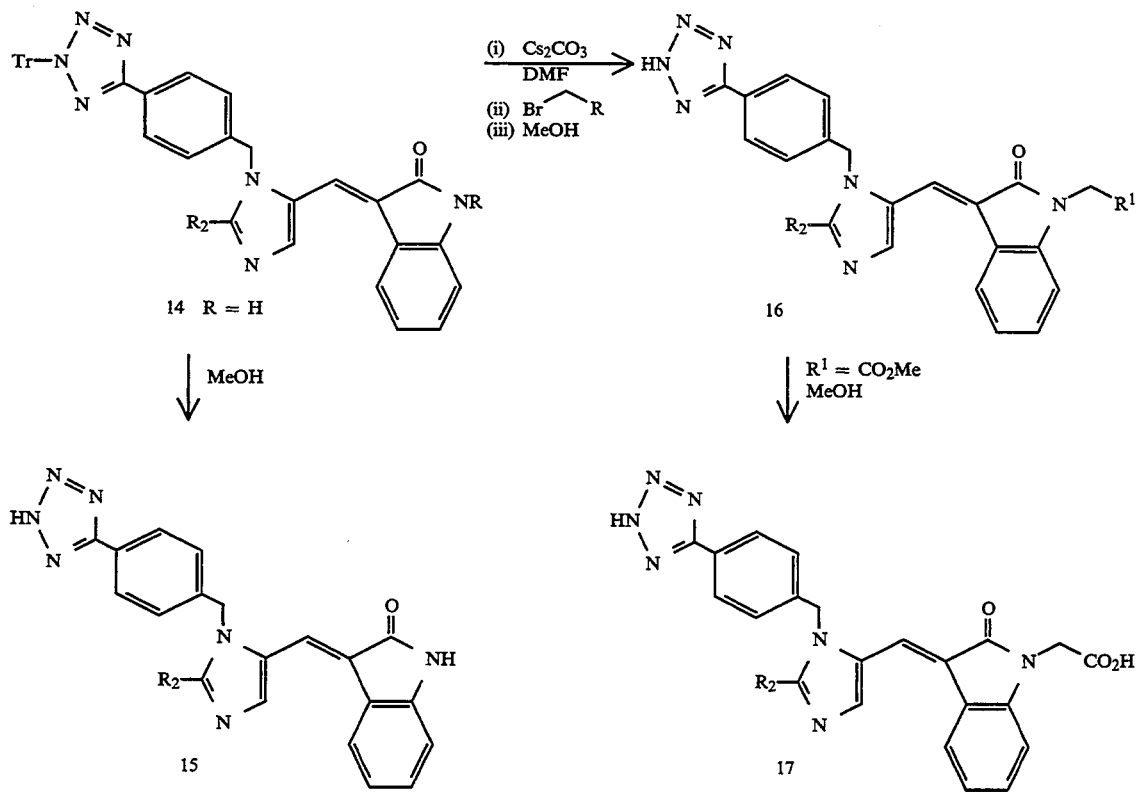
SCHEME IX
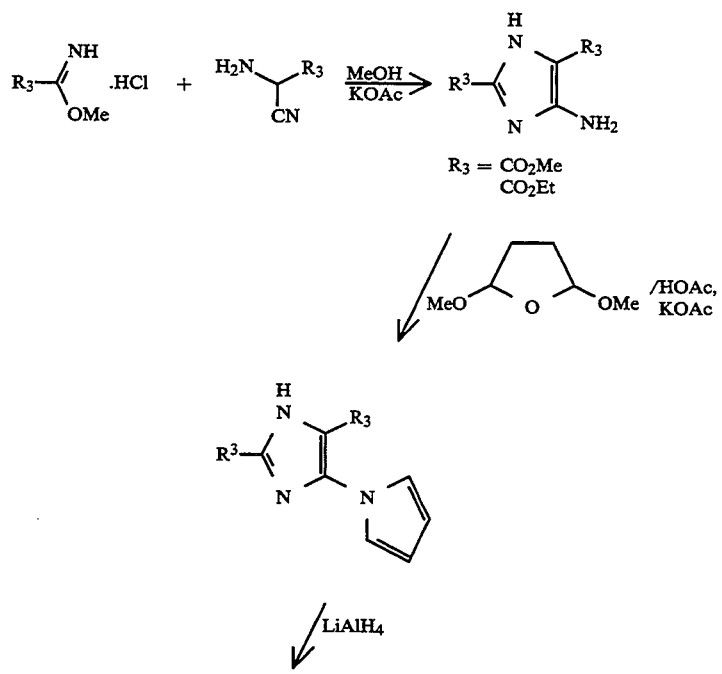

SCHEME IX

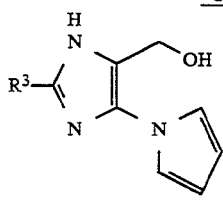

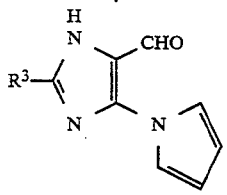

18

SCHEME X

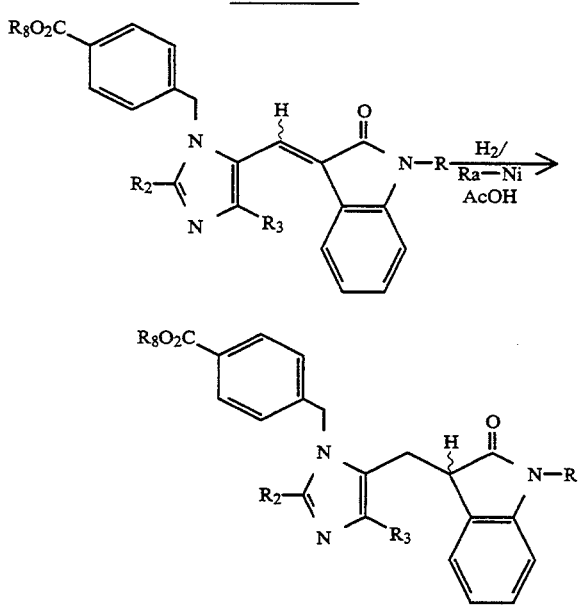

For preparing pharmaceutical compositions from the compounds described by this invention, inert, pharmaceutically acceptable carriers can be either solid or liquid. Solid form preparations include powders, tablets, dispersible granules, capsules, cachets, and suppositories. A solid carrier can be one or more substances which may also act as diluents, flavoring agents, solubilizers, lubricants, suspending agents, binders, or tablet disintegrating agents. It can also be encapsulating material. In powders, the carrier is a finely divided solid which is in admixture with the finely divided active compound. In the tablet the active compound is mixed with a carrier having the necessary binding properties in suitable proportions and compacted in the shape and size desired. The powders and tablets preferably contain from 5 to 10% to about 70% of the active ingredient. Suitable solid carriers are magnesium carbonate, magnesium stearate, talc, sugar, lactose, pectin, dextrin, starch, gelatin, tragacanth, methylcellulose, a low melting wax, cocoa butter, and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets, and capsules can be used as solid dosage forms suitable for oral administration.

The compounds of the present invention may be administered orally, buccally, parentsrally, by inhalation spray, rectally, or topically in dosage unit formulations containing conventional nontoxic pharmaceutically acceptable carriers, adjuvants, and vehicles as desired. The term parenteral as used herein includes subcutaneous injections, intravenous, intramuscular, intrasternal injection, or infusion techniques.

For preparing suppositories, a low melting wax such as a mixture of fatty acid glycerides or cocoa butter is first melted, and the active ingredient is dispersed homogeneously therein by stirring. The molten homogeneous mixture is then poured into convenient sized molds, allowed to cool, and thereby solidify.

Liquified form preparations include solutions, suspensions, and emulsions. As an example may be mentioned water or water/propylene glycol solutions for parenteral injection. Liquid preparations can also be formulated in solution in aqueous polyethyleneglycol solution. Aqueous suspensions suitable for oral use can be made by dispersing the finely divided active component in water with viscous material, i.e., natural or synthetic gums, resins, methylcellulose, sodium carboxymethylcellulose, and other well-known suspending agents.

Also included are solid form preparations which are intended to be converted, shortly before use, to liquid form preparations for either oral or parenteral administration. Such liquid forms include solutions, suspensions, and emulsions. These particular solid form preparations are most conveniently provided in unit dose form and as such are used to provide a single liquid dosage unit. Alternately, sufficient solid may be provided so that after conversion to liquid form, multiple individual liquid doses may be obtained by measuring predetermined volumes of the liquid form preparation as with a syringe, teaspoon, or other volumetric container. When multiple liquid doses are so prepared, it is preferred to maintain the unused portion of said liquid doses at low temperature (i.e., under refrigeration) in order to retard possible decomposition. The solid form preparations intended to be converted to liquid form may contain, in addition to the active material, flavorants, colorants, stabilizers, buffers, artificial and natural sweeteners, dispersants, thickeners, solubilizing agents, and the like. The liquid utilized for preparing the liquid form preparation may be water, isotonic water, ethanol, glycerin, propylene glycol, and the like, as well as mixtures thereof. Naturally, the liquid utilized will be chosen with regard to the route of administration, for example, liquid preparations containing large amounts of ethanol are not suitable for parenteral use.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules, and powders in vials or ampules. The unit dosage form can also be a capsule, cachet, or tablet itself, or it can be the appropriate number of any of these in packaged form.

The quantity of active compound in a unit dose of preparation may be varied or adjusted from 1 to 500 mg, preferably 5 to 100 mg according to the particular application and the potency of the active ingredient. The compositions can, if desired, also contain other compatible therapeutic agents.

In therapeutic use as antihypertensive agents, the mammalian dosage range for a 70 kg subject is from 0.1 to 500 mg/kg of body weight per day or preferably 1 to 500 mg/kg of body weight per day optionally in divided portions. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter the dosage is increased by small increments until the optimum effect under the circumstances is reached. For convenience, the total daily dosage may be divided and administered in portions during the day if desired.

The effectiveness of the compounds of the instant invention is determined by a test (RBAT$_1$) entitled Receptor Binding of Angiotensin II. In this in vitro test the inhibition of tritiated angiotensin II binding to rat liver membranes is measured (Dudley D T, et al, *Molecular Pharmacology* 1990;38:370–7).

| Example Name | RBAT$_1$ IC$_{50}$, nM | Example Name | RBAT$_1$ IC$_{50}$, nM |
| --- | --- | --- | --- |
| 1D | 75 | 4C | 358 |
| 2B | 610 | 4E | 72 |
| 2C | 201 | 4E | 72 |
| 2D | 86 | 4F | 256 |
| 2F | 67 | 4G | 64 |
| 2G | 746 | 4H | 226 |
| 3 | 170 | 4I | 300 |
| 3A | 140 | 4J | 686 |
| 3B | 120 | 4K | 110 |
| 3C | 22 | 4M | 54 |
| 3F | 123 | 5 | 94 |
| 3G | 20 | 6 | 25 |
| 3H | 52 | 6A | 12 |
| 3I | 140 | 7 | 5.7 |
| 4 | 590 | 8 | 47 |

-continued

| Example Name | RBAT$_1$ IC$_{50}$, nM | Example Name | RBAT$_1$ IC$_{50}$, nM |
| --- | --- | --- | --- |
| 4A | 640 | 9 | 98 |
| 4B | 95 | 10 | 53 |

Based on the observations that ACE inhibitors are known to benefit patients with heart failure, the instant compound which also interrupts the renin angiotensin system (RAS), would show similar benefits.

The following examples are provided to enable one skilled in the art to practice the present invention. These examples are not intended in any way to limit the scope of the invention but are illustrative thereof.

EXAMPLE 1

Ethyl 4-[[2-butyl-5-[(1,2-dihydro-2-oxo-3H-indol-3ylidene)-methyl]-1H-imidazol-1-yl]methyl]benzoate A mixture of 0.8 9 (2.85 mmol) of 2-butyl-1-(4-carbethoxy)benzyl-5-formyl-imidazole, 0.3 9 (2.85 mmol) of oxindole and β-alanine (20 m$_9$) in AcOH (15 mL) was heated at reflux for 18 hours. AcOH was distilled off and the residue was treated with EtOAc. The solid (09.7 g) was filtered off and recrystallized from EtOAc to give 0.27 g of yellow solid (E-isomer), mp 272°–273° C.

Analysis calculated for C$_{26}$H$_{27}$N$_3$O$_3$: C, 72.71; H, 6.34; N, 9.78. Found: C, 72.52; H, 6.41; N, 9.75. MS (CI) 430 (m). Second crop; (Z-isomer); 0.3 g; mp 169°–171° C. Analysis Found: C, 72.62; H, 6.42; N, 9.54. MS (CI) 430 (m). H NMR indicate the presence of 15% of E-isomer.

The following were prepared using the procedure described above.

EXAMPLE 1A

Methyl 4-[[2-butyl-5-[(1,2-dihydro-2-oxo-3H-indol-3-ylidene)-methyl]-1H-imidazol-1-yl]methyl]-3-chlorobenzoate E-isomer; mp 219°–220° C.; MS (CI) 450 (m). Analysis calculated for C$_{25}$H$_{24}$ClN$_3$O$_3$.H$_2$O: C, 65.43; H, 5.49; N, 9.16. Found: C, 65.43; H, 5.27; N, 9.08.

Z-isomer; mp 195°–196° C.; MS (CI) 450 (m). Calculated for C$_{25}$H$_{24}$ClN$_3$O$_3$.0.3 H$_2$O: C, 65.95; H, 5.46; N, 9.15. Found: C, 65.95; H, 5.46; N, 9.15.

EXAMPLE 1B

Methyl 4-[[2-butyl-5-[(1,2-dihydro-5-methyl-2-oxo-3H-indol-3-ylidene)methyl]-1H-imidazol-1-yl]methyl]benzoate Mixture of E- and Z-isomers; MS (CI) 430 (m). Analysis calculated for C$_{26}$H$_{27}$N$_3$O$_3$: C, 72.71; H, 6.34; N, 9.78. Found: C, 72.47; H, 6.21; N, 9.56. mp 195°–200° C.

EXAMPLE 1C

Ethyl 4-[[2-butyl-4-chloro-5-[(1,2-dihydro-6-methyloxo-3H-indol-3-ylidene)methyl]-1H-imidazol-1-yl]methyl]benzoate Mixture of E- and Z-isomer; MS (CI) 478 (m). Analysis calculated for C$_{27}$H$_{28}$ClN$_3$O$_3$: C, 67.85; H, 5.90; N, 8.79. Found: C, 67.41; H, 6.07; N, 8.52.

EXAMPLE 1D

Methyl 4-[[2-propyl-5-[(1,2-dihydro-1-methyl-2-oxo-3H-indol-3-ylidene)methyl]-1H-imidazol-1-yl]methyl]benzoate E-isomer; mp 181°–182° C.; MS (CI) 415 (m). Analysis calculated for $C_{25}H_{25}N_3O_3$: C, 72.27; H, 6.06; N, 10.11. Found: C, 72.22; H, 5.94; N, 9.97.

Z-isomer; MS (CI) 415 (m); mp 146°–148° C. Analysis calculated for $C_{25}H_{25}N_3O_3 \cdot 0.53\ H_2O$: C, 70.68; H, 6.18; N, 9.89. Found: C, 70.65; H, 6.16; N, 9.82.

EXAMPLE 1E

Methyl 4-[[2-butyl-5-[(1,2-dihydro-4-methyl-2-oxo-3H-indol-3-ylidene)methyl]-1H-imidazol-1-yl]methyl]benzoate Z-isomer; mp 205°–207° C.; MS (CI) 430 (m). Analysis calculated for $C_{26}H_{27}N_3O_3$: C, 72.71; H, 6.34; N, 9.78. Found: C, 72.25; H, 6.13; N, 9.56.

EXAMPLE 1F

Methyl 4-[[2-butyl-5-[(1,2-dihydro-7-methyl-2-oxo-3H-indol-3-ylidene)methyl]-1H-imidazol-1-yl]methyl]benzoate E-isomer; mp 198°–200° C.; MS (CI) 430 (m). Analysis calculated for $C_{26}H_{27}N_3O_3$: C, 72.71; H, 6.34; N, 9.78. Found: C, 72.33; H, 6.21; N, 9.63.

Z-isomer; mp 221°–223° C.; MS (CI) 430 (m). Analysis calculated for $C_{26}H_{27}N_3O_3$: C, 72.71; H, 6.34; N, 9.78. Found: C, 72.67; H, 6.13; N, 9.88.

EXAMPLE 1G

Methyl 4-[[2-butyl-5-[(5-chloro-1,2-dihydro-2-oxo-3H-indol-3-ylidene)methyl]-1H-imidazol-1-yl]methyl]benzoate Z-isomer; mp 238°–241° C.; MS (CI) 450 (m). Analysis calculated for $C_{25}H_{24}ClN_3O_3 \cdot 0.25\ EtOAc$: C, 66.17; H, 5.55; N, 8.90. Found: C, 65.77; H, 5.45; N, 9.02.

EXAMPLE 1H

Methyl 4-[[2-butyl-5-[(1,2-dihydro-7-methoxy-2-oxo-3H-indol-3-ylidene)methyl]-1H-imidazol-1-yl]methyl]benzoate E-isomer; MS (CI) 446 (m).

Z-isomer; mp 190°–195° C.; MS (CI) 446 (m). Analysis calculated for 0.45 EtOAc: C, 68.82; H, 6.36; N, 8.66. Found: C, 68.58; H, 5.94; H, 8.36.

EXAMPLE 1I

Ethyl 3.-[[2-butyl-1-[[4-(methoxycarbonyl)phenyl]methyl]-1H-imidazol-5-yl]methylene]-2,3-dihydro-2-oxo-1H-indole-5-carboxylate Z-isomer; MS (CI) 488 (m); mp 211°–215° C. Analysis calculated for: C, 68.98; H, 6.00; N, 8.62. Found: C, 68.64; H, 6.11; N, 8.49.

EXAMPLE 2

Ethyl 4-[[2-butyl-4-chloro-5-[(1,2-dihydro-2-oxo-3H-indol-3-ylidene)methyl]-1H-imidazol-1-yl]methyl]benzoate A mixture of 0.87 g (2.5 mmol) of 2-butyl-1-(4-carbethoxy)benzyl-4-chloro-5-formyl-imidazole), 0.33 g (2.5 mmol) of oxindole and 0.1 mL of piperidine in toluene (30 mL) was heated at reflux with a Dean-Stark apparatus for 24 hours. The solution was diluted with toluene, washed with water, dried, and stripped to give a dark brown solid. This was purified via column chromatography (silica gel, hexane/ethyl acetate, 10% to 50%) to yield 0.75 g of a dark yellow foam.

MS (CI) 464 (m). Analysis calculated for $C_{26}H_{26}ClN_3O_3$: C, 67.31; H, 5.65; N, 9.06. Found: C, 67.65; H, 5.58; N, 8.99. $^1H$ NMR indicate a mixture of E-/Z-isomer ratio of 4/1.

EXAMPLE 2A

Ethyl 3-[[2-butyl-1-(4-methoxycarbonyl)phenyl]methyl]-1H-imidazol yl]methylene]-2,3-dihydro-2-oxo-1H-indole-1-acetate Z(83%)/E(17%); mp 233°–235° C.; MS (CI) 502 (m). Analysis calculated for $C_{29}H_{31}N_3O_5 \cdot 0.72\ H_2O$: C, 67.67; H, 6.36; N, 8.15. Found: C, 67.66; H, 6.52; N, 8.15.

E(89%)/Z(11%); mp 200°–201° C.; MS (CI) 502 (m). Analysis calculated for $C_{29}H_{31}N_3O_5$: C, 69.44; H, 6.23; N, 8.38. Found: C, 69.10; H, 6.34; N, 8.29.

EXAMPLE 2B

Methyl 4-[[(2-propyl-5-[1,2-dihydro-1-(methylaminocarbonyl)-2-oxo-3H-indol-3-ylidene]methyl]-1H-imidazol-1-yl]methyl benzoate Z(78%)/E(22%); MS (FAB) 459 (m); mp 76°–80° C. Analysis calculated for $C_{26}H_{26}N_4O_4 \cdot 0.31\ H_2O$: C, 67.29; H, 5.78; N, 12.07. Found: C, 67.30; H, 5.82; N, 11.99.

E(71%)/Z(29%); MS (CI) 459 (m); mp 73°–76° C. Analysis calculated for $C_{26}H_{26}N_4O_4 \cdot 0.4\ H_2O$: C, 67.05; H, 5.80; N, 12.03. Found: C, 67.05; H, 5.89; N, 11.91.

EXAMPLE 2C

Methyl 4-[[2-butyl-5-[1,2-dihydro-1-hydroxy-2-oxo-3H-indol-3-ylidene)methyl]-1H-imidazol-1-yl]methyl]benzoate Mixture of E- and Z-isomers. A mixture of the aldehyde (0.488 g; 1.63 mM) and N-hydroxyoxindole (Kende AS, et al, *Synthetic Comm* 1990;20:2133) (0.25 g; 1.68 mM) in abs. EtOH (6.0 mn) is treated with 4 drops of piperidine and the solution is heated to reflux for 4.0 hours. On cooling, the product crystallizes containing ethanol as solvent of crystallization. Yield 0.473 g (62.7%); mp 198°–200° C.

MS (CI) 432 (m).

EXAMPLE 2D (E)-4-[[5-[(1,2-dihydro-2-oxo-3H-indol-3-ylideny)methyl]-2-propyl-4-(1H-pyrrol-1-yl)-1H-imidazol-1-yl]methyl]benzoic acid MS (FAB) 453 (m). Analysis calculated for $C_{27}H_{22}N_4O_3Na_2 \cdot 0.43\ H_2O$: C, 64.32; H, 4.57; N, 11.11. Found: C, 64.70, H, 4.97; N, 10.77.

EXAMPLE 2E

Methyl-4-[[2-butyl-5-[1,2-dihydro-2-oxo-3H-indol-3ylidene)methyl]-1H-imidazol-1-yl]methyl]benzoate MS (CI) 416 (m); mp 264°–265° C.

EXAMPLE 2 F

Benzoic acid, 4-[[5-[[2,3-dihydro-1-(1-methylethyl)-2-oxo-1H-indol-3-ylidene]methyl]. -2-propyl-1H-imidazol-1-yl]methyl]-, methyl ester, (Z)

By following the methodology of Example 2 and substituting the properly substituted oxindole in place of oxindole additional analogs were obtained.

MS (CI) 444 (m); Analysis calculated for $C_{27}H_{29}N_3O_3.0.5$ tBuOH·0.4 $H_2O$: C, 71.89; H, 6.72; N, 9.25; Found: C, 71.94; H, 6.77; N, 9.10.

EXAMPLE 2G

Methyl 4-[[5-[(1,2-dihydro-2-oxo-1-propyl-3H-indol-3-ylidenyl)methyl]-2-propyl -1H-imidazol-1-yl]methyl]-benzoate MS (CI) 444 (m). Analysis calculated for $C_{27}H_{29}N_3O_3.0.5$ $H_2O$: C, 71.66; H, 6.68; N, 9.29. Found: C, 71.64, H, 6.55; N, 9.19.

EXAMPLE 2H

Benzoic acid, 4-[[5-[(2,3-dihydro-2-oxo-1H-indol-3ylidene)methyl]-2-ethyl-4-methyl-1H-imidazol-1-yl]methyl]-(E)

By replacing the 5-formyl-imidazole in Example 2 with the 5-formyl-imidazole from Example 11D and following the methodology described in Example 2, the title compound was obtained. MS (CI) 387, (m).

Analysis calculated for $C_{23}H_{21}N_3O_3.0.8$ $H_2O$: C, 68.75; H, 5.67; N, 10.46. Found: C, 68.51; H, 5.53; N, 10.13. $^1H$ NMR indicate 10% of the Z-isomer.

EXAMPLE 3

4-[[2-Butyl-5-[(1,12-dihydro-2-oxo-3H-indol-3-ylidene)-methyl]-1H-imidazol-1-yl]methyl]benzoic acid A mixture of 0.4 g of compound 1 (E- and Z-isomer, Example 1) in methanol (10 mL) and a solution of 80 mg of NaOH in 0.35 mL of water was heated at reflux for 4 hours. Methanol was stripped and the solution was diluted with water and extracted with EtOAc. The aqueous solution was acidified to pH 4 and the solid was filtered, washed with water, and dried in a vacuum oven at 80° C. for 14 hours to give 0.35 g of the product, mp 237°–238° C.; MS (CI) 401 (m).

Analysis calculated for $C_{24}H_{23}N_3O_3$: C, 71.80; H, 5.77; N, 10.47. Found: C, 66.98; H, 5.66; N, 10.25.

The following were prepared by using the procedure described above.

EXAMPLE 3A (E)-4-[[2-Butyl-4-chloro-5-[(1,2-dihydro-2-oxo-3H-indol-3-ylidene)]-1H-imidazol-1-yl]methyl]benzoic acid MS (CI) 436 (m); crystallized from EtOAc to give analytically pure sample, mp 241°–242° C. Analysis calculated for $C_{24}H_{22}ClN_3O_3$: C, 66.13; H, 5.09; N, 9.64; $Cl$, 8.13. Found: C, 65.75; H, 5.06; N, 9.45; Cl, 8.20.

EXAMPLE 3B

4-[[2-Butyl-5-[(1,2-dihydro-7-methoxy -2-oxo-3H-indol-3-ylidene)methyl]-1H-imidazol-1-yl]methyl]benzoic acid E-and Z-isomer (1:1); MS (CI) 432 (m); mp 248°–251° C. Analysis calculated for $C_{25}H_{25}N_3O_4.0.8$ $H_2O$: C, 67.34; H, 6.01; N, 9.42. Found: C, 67.06; H, 5.98; N, 9.25.

EXAMPLE 3C

3-[[2-Butyl-1-[(4-carboxyphenyl)methyl]-1H-imidazol-5-yl]methylene]-2,3-dihydro-2-oxo-1H-indole-1-acetic acid E-and Z-mixture (1:1); MS (EI) 460 (m). Analysis calculated for $C_{26}H_{25}N_3O_5.1.28$ $H_2O$: C, 64.74; H, 5.50; N, 8.51.

EXAMPLE 3D

3-[[2-Butyl-1-[(4-carboxyphenyl)methyl]-1H-imidazol-5yl]methylene]-2,3-dihydro-2-oxo-1H-indole-5-carboxylic acid E- and Z-isomer (1:1); MS (EI) 445 (m). Analysis calculated for $C_{25}H_{23}N_3O_5.0.81$ $H_2O$: C, 65.27; H, 5.39; N, 9.13. Found: C, 65.26; H, 5.33; N, 9.15.

EXAMPLE 3E

4-[[2-Butyl-5-[(1,2-dihydro-5-methyl-2-oxo-3H-indol-3-ylidenemethyl]-1H-imidazol-1-yl]methyl]benzoic acid E-and Z-isomer (1:1); MS (CI) 416 (m). Analysis calculated for $C_{25}H_{25}N_3O_3.1.65$ $H_2O$: C, 67.44; H, 6.41; N, 9.44. Found: C, 67.15; H, 6.02; N, 9.36.

EXAMPLE 3 F

4-[[2-Butyl-5-[(1,2-dihydro-1-methyl-2-oxo-3H-indol-3-ylidene)methyl]-1H-imidazol-1-yl]methyl]benzoic acid Mixture of E- and Z-isomers. A mixture of the ester from Example 2C (126 mg; 0.27 mM), MeOH (10 mL), and water (10 mL) is treated with 1 N NaOH (1.5 mL) when the mixture turns into a dark solution. The solution is heated on a steam bath for 5 minutes and is then concentrated to a small volume, diluted with water, and filtered. The aqueous solution is carefully acidified with acetic acid (1.5 mL) when the product slowly crystallizes out as mono hydrate. It is filtered, washed with water, and dried. Yield 119 mg (99%); mp 185°–188° C. MS (FAB) 418 (M+1).

Analysis calculated for $C_{24}H_{23}N_3O_4.1$ $H_2O$: C, 66.19; H, 5.79; N, 9.65. Found: C, 66.32; H, 5.67; N, 9.60.

EXAMPLE 3G

1H-Indole-1-propanoic acid, 3-[[2-butyl-1-[(4-carboxyphenyl)methyl]-1H-imidazol-5-yl]methylene]-2,3-dihydro-2-oxo -, (E)

MS (CI) 474 (m). Analysis calculated for $C_{27}H_{27}N_3O_5.0.9$ $H_2O$: C, 66.22; H, 5.93; N, 8.58. Found: C, 66.30; H, 5.82; N, 8.32.

EXAMPLE 3H

4-[[2-butyl-5-[(1-butyl-1,2-dihydro-2-oxo-3H-indol-3-ylidenyl)methyl]-1H-imidazol-1-yl]methyl]-3 chlorobenzoic acid MS (FAB) 492 (m). Analysis calculated for $C_{28}H_{30}ClN_3O_3.CH_2Cl_2.2.5$ $H_2O$: C, 56.00; H, 6.00; N, 6.76. Found: C, 55.74; H, 5.99; N, 6.46.

EXAMPLE 3I

4-[[5-[(1,2-dihydro-2-oxo-1-propyl-3H-indol-3-ylidenyl)methyl]-2-propyl-1H-imidazol-1-yl]methyl]-benzoic acid (FAB) 416 (m).

EXAMPLE 4

Benzoic acid,
4-[[5-[(1-butyl-2,3-dihydro-2-oxo-1H-indol-3-ylidene)-methyl]-2=propyl-4=(1H-pyrrol-1-yl)-1H-imidazol-1-yl]methyl]-, methyl ester, (E)

To a solution of 0.46 g (1 mmol) of the methylester of compound from Example 2D in DMF (6 mL) was added $CS_2CO_3$ (0.65 g, 2 mmol). This reaction mixture was stirred for 15 minutes followed by the addition of a solution of nBuBr (0.27 g, 2 mmol) in DMF (5 mL). The solution was stirred for 5 hours at room temperature. DMF was distilled under high vacuum, the residue was dissolved in water and the solution was extracted with EtOAc. The extract was washed with water, dried, and stripped. The residue was triturated with ether/EtOAc to yield a solid which was filtered to give 0.35 g of the titled product, MS 523 (m), mp 135°–136° C.

Analysis calculated for $C_{32}H_{34}N_4O_3$: C, 73.54; H, 6.56; N, 10.72. Found: C, 73.05; H, 6.51; N, 10.40.

The following were prepared by using the methodology described above.

EXAMPLE 4A

Benzoic acid,
4-[[5-[(2,3-dihydro-1-methyl-2-oxo-1H-indol-3-ylidene)methyl]-2-propyl-4-(1H-pyrrol-1-yl)-1H-imidazol-1-yl]methyl]-, methyl ester, (E)

MS (CI) 481 (m); mp 163°–164° C. Analysis calculated for $C_{29}H_{28}N_4O_3.0.29\ CH_2Cl_2$: C, 69.64; H, 5.70; N, 11.09. Found: C, 70.02; H, 6.02; N, 10.70.

EXAMPLE 4B

1H-Indole-1-acetic acid,
2,3-dihydro-3-[[1-[[4-(methoxycarbonyl)phenyl]methyl]-2-propyl-4-(1H-pyrrol-1-yl)-1H-imidazol-5-yl]methylene]-2-oxo-, methyl ester, (E)

Yellow foam; MS (CI) 539 (m). Analysis calculated for $C_{31}H_{30}N_4O_5.0.64\ EtOAc$: C, 67.75; H, 5.62; N, 9.61. Found: C, 67.36; H, 5.62; N, 9.42.

Replacing compound from Example 2D with 2E, and following the procedure of Example 4 using requisite alkyl halide additional analogs have been prepared.

EXAMPLE 4C

Benzoic acid,
4-[[2-butyl-5-[(1-butyl-2,3-dihydro-2-oxo-1H-indol-3-ylidene)methyl]-1H-imidazol-1-yl]methyl]-, methyl ester Yellow foam; MS (CI) 472 (m). Analysis calculated for $C_{29}H_{33}N_3O_3.0.1\ EtOAc$: C, 73.50; H, 7.09; N, 8.75. Found: C, 73.17; H, 7.26; N, 8.78.

EXAMPLE 4D

Benzoic acid,
4-[[2-butyl-5-[[1-[2-(dimethylamino)ethyl]-2,3-dihydro-2-oxo-1H-indol-3-ylidene]methyl]-1H-imidazol-1-yl]methyl]-, methyl ester, (E)

Mixture of E and Z-isomers; MS (CI) 487 (m). Analysis calculated for: $C_{29}H_{34}N_4O_3.0.73\ CH_3OH$: C, 70.02; H, 7.30; N, 10.99. Found: C, 70.25; H, 7.13; N, 10.59.

EXAMPLE 4E

1H-Indole-1-propanoic acid, 3-[[2-butyl-1-[[4-(methoxycarbonyl)phenyl]methyl]-1H-imidazol-5-yl]methylene]-2,3-dihydro-2-oxo, ethyl ester. (E)

MS (CI) 516 (m). Analysis calculated for $C_{30}H_{33}N_3O_5.0.44\ MeOH$: C, 69.02; H, 6.61; N, 7.93. Found: C, 68.76; H, 6.33; N, 7.99.

EXAMPLE 4F

Benzoic acid,
4-[[2-butyl-5-[[1-[(4-chlorophenyl)methyl]-2,3-dihydro-2-oxo-1H-indol-3-ylidene]methyl]-1H-imidazol-1-yl]methyl]-, (E)

MS (CI) 526 (m). Analysis calculated for $C_{31}H_{28}N_3O_3Cl.0.2\ H_2O$: C, 70.30; H, 5,40; N, 7.93. Found: C, 70.27; H, 5.45, N, 8.03.

EXAMPLE 4G

Benzoic acid.
4-[2-butyl-5-[[2,3-dihydro-1-(2-methoxy-2-oxoethoxy)-2-oxo-1H-indol-3-ylidene]methyl]-1H-imidazol-1-yl]methyl]-, methyl ester By substituting compound from Example 2D with compound 2C in Example 4 and using methyl bromoacetate, the above target compound was obtained.

MS (CI) 504 (m). Analysis calculated for $C_{28}H_{29}N_3O_6.0.5\ H_2O$: C, 66.79; H, 5.80; N, 8.34. Found: C, 65.61; H, 5.90; N, 8.20.

EXAMPLE 4H

Benzoic acid,
4-[[2-butyl-5-[[1-(cyanomethyl)-2,3-dihydro-2-oxo-1H-indol-3-ylidene]methyl]-1H-imidazol-1-yl]methyl]-, methyl ester, (E)

Z-isomer; MS (CI) 455 (m) ; mp 193°–195° C. Analysis calculated for $C_{27}H_{26}N_4O_3$: C, 71.35; H, 5.77; N, 12.33. Found: C, 71.04; H, 5.71; N, 12.15.

E-isomer; MS (CI) 455 (m) ; mp 124°–127° C. Analysis calculated for $C_{27}H_{26}N_4O_3$: C, 71.35; H, 5.77, N, 12.33. Found: C, 71.04; H, 5.63, N, 12.11.

EXAMPLE 4I

Ethyl
(Z)-(±)-2,3,dihydro-3-[[3-[[4-(methoxycarbonylphenyl]methyl]-2-propyl-3H-imidazol-4-yl]methylene]-4-methyl-2-oxo-α-propyl-1H-indole-1-acetate By substituting compound from Example 2D with compound 1E in Example 4 and using ethyl 2-bromopentanoate, the title compound was obtained. MS (CI) 544 (m); mp 154°–156° C.

Analysis calculated for $C_{32}H_{37}N_3O_5$: C, 70.70; H, 6.86; N, 7.73. Found: C, 70.38; H, 6.93; N, 7.55.

EXAMPLE 4J

Methyl
(Z)-2,3-dihydro-3-[[3-[[4-methoxycarbonylphenyl]methyl]-2-propyl-3H-imidazol-4-yl]methylene]-4 -methyl-2-oxo-1H-indole-1-acetate By substituting compound from Example 2D with compound 1E in Example 4 and using methyl bromoacetate, the title compound was obtained. MS (CI) 488 (m); mp 228°–230° C.

Analysis calculated for $C_{28}H_{29}N_3O_5.1.2\ H_2O$: C, 66.05; H, 6.22; N, 8.27. Found: C, 65.85; H, 5.93; N, 7.97.

EXAMPLE 4K

Methyl 4-[[2-butyl-5-[(1-butyl-1,2-dihydro-2-oxo-3H-indol-3-yliden)methyl]-1H-imidazolyl]methyl]-3-chlorobenzoate By substituting compound from Example 2D with compound 1A in Example 4, the above compound was obtained. MS (CI) 505 (m).

EXAMPLE 4L

Ethyl (Z)-3-[[2-butyl-3-[[4-(methoxycarbonyl)phenyl]methyl]-3H-imidazol-4-yl]methylene]-2,3-dihydro-7-methoxy-2-oxo-1H-indole-1-acetate By substituting compound from Example 2D with compound 1H in Example 4, and using ethyl bromoacetate, the title compound was obtained.

MS (CI) 532, (m), mp 157°–158° C. Analysis calculated for $C_{30}H_{33}N_3O_6.0.34$ MeOH: C, 67.17; H, 6,38; N, 7.90. Found: C, 66.78; H, 6.15; N, 7.72.

The following compounds have been prepared by methods similar to those above:

4-[[2-butyl-5-[(1,2-dihydro-7-methyl-2-oxo-3H-indol-3-ylidenyl)methyl]-1H-imidazol-1-yl]methyl]benzoic acid Methyl 4-[[5-[(1,2-dihydro-1-methyl-2-oxo-3H-indol-3-ylidenyl)methyl]-2-propyl-1H-imidazol-1yl]methyl]benzoate Methyl 2,3-dihydro-3-[[3-[[4-(methoxycarbonyl) phenyl]methyl]-2-propyl-3H-imidazol-4-yl]methylene]-2-oxo-1H-indole-7-acetate

EXAMPLE 5

Benzoic acid, 4-[[2-butyl-5-[[2,3-dihydro-2-oxo-1-(1H-tetrazol-5-ylmethyl)-1H-indol-3-ylidene]methyl]-1H-imidazol-1-yl]methyl]-, methyl ester, (E)

A mixture of 0.5 g (1.1 mM) of the nitrile from Example 4H, NaN$_3$ (0.14 g, 2.2 mM) and 0.12 g (NH$_4$Cl) in DMF (10 mL) was heated at 95° C. for 4.5 hours. DMF was distilled under vacuum and the residue was treated with water. The solution was adjusted to pH 2 when an orange colored solid precipitated. It was filtered, washed successively with water and ether, and finally air-dried to give 0.38 g of a solid. $^1$H NMR indicate mostly Z-isomer. HPLC indicate a mixture of 82% (Z)- and 15% (E)-isomer. MS (CI) 498 (m). The filtrate was adjusted to pH 5 and the solid was filtered, washed with successively with water and ether, and air-dried to give 50 mg of a yellow solid. $^1$HNMR idicate mostly E-isomer. HPLC indicate a mixture of 82.5% (E)- and 4.6% (Z)-isomer. MS (CI) 498 (m).

EXAMPLE 6

1H-Indole-1-acetic acid, 3-[[2-butyl-1-[[4-(1H-tetrazol-5-yl)phenyl]methyl]-1H-imidazol-5yl]methylene]-2,3-dihydro-2-oxo-, methyl ester A mixture of 3.58 g (6.5 mmol) of the compound from Example 14, oxindole (0.91 g, 6.8 mmol) and piperidine (0.1 g) in toluene (35 mL) was heated under reflux for 18 hours under N$_2$. The reaction mixture was cooled and filtered to give a solid. The filtrate was evaporated to remove toluene. This residue was combined with the solid and chromatographed [CH$_2$Cl$_2$CH$_2$Cl$_2$/EtOAc(1:1)]to separate E-(2.1 g) and Z-isomer (1.2 g) of the desired product. 3-[[2-butyl-3-[[4-[2-(triphenylmethyl)-2H-tetrazol-5-yl]phenyl]methyl]-3H-imidazol-4-yl]methylene]-1,3-dihydro-2H-indol-2-one A mixture of 0.45 g (0.67 mmol) of the above oxindole, CS$_2$CO$_3$(4.79 g, 14.7 mmol) and methyl bromoacetate ( (0.11 g, 0.7 mmol) in DMF (10 mL) was stirred at room temperature for 2 hours. Upon usual work up and purification [chromatography, CH$_2$Cl$_2$/Hexane (10%) —CH$_2$Cl$_2$/EtOAc(20%)]gave 0.9 g of the target compound. Methyl 3-[[2-butyl-3-[[4-[2-(triphenylmethyl)-2H-tetrazol-5-yl]phenyl]methyl]-3H-imidazol-4-yl]methylene]-2,3-dihydro-2-oxo-1H-indol-1-acetate A solution of the above trityltetrazole compound (0.9 g) in MeOH (12 mL) was heated under reflux for 16 hours. The reaction mixture was cooled to 0° C. and filtered. The residue was washed with small volume of methanol and air-dried to give the tetrazole derivative (0.4 g). MS (CI) 498 (m) , mp 222°–231° C.

Analysis calculated for $C_{27}H_{27}N_7O_3.0.6$ H$_2$O: C, 63.79; H, 5.59; N, 19.29. Found: C, 64.19; H, 5.42; N, 18.82.

EXAMPLE 6A

1H-Indole-1-acetic acid, 3-[[2-butyl-1-[[4-(1H-tetrazol-5-yl)phenyl]methyl]-1H-imidazol-5yl]methylene]-2,3-dihydro-2-oxo-, ethyl ester The title compound was analogously prepared. (CI) 511 (m); mp 185°–188° C.

Analysis calculated for $C_{28}H_{29}N_7O_3.0.63$ H$_2$.0.51 EtOAc; C, 63.55; H, 6.11; N, 17.24. Found: C, 63.54; H, 5.81; N, 17.23.

EXAMPLE 7

3-[[2-butyl-3-[[4-(1H-tetrazol-5-yl) phenyl]methyl]-3H-imidazol-4-yl]methylene]-2,3-dihydro-2-oxo-1H-indole-1-acetic acid The compound from Example 6 was suspended in MeOH (8 mL) to which was added a solution of dilute NaOH (0.103 g in 1 mL H$_2$O). The clear solution was stirred at room temperature for 2 hours. MeOH was removed, the residue was diluted with water, and the solution adjusted to pH 4. The precipitate was filtered, washed with small volume of water, and dried under vacuum at 80° C. for 3.5 hours. $^1$H NMR indicate a 1:1 mixture of E- and Z-isomer of the desired product.

MS (CI) 484 (m), mp 212°–215° C. Analysis calculated for $C_{26}H_{25}N_7O_3.0.74$ H$_2$O: C, 63.03; H, 5.19; N, 19.34. Found: C, 62.85; H, 5.37%; N, 19.73.

EXAMPLE 8

2(1H)-Isoquinolineacetic acid, 3,4-dihydro-4-[[1-[[4-(methoxycarbonyl)phenyl]methyl]-2-propyl-1H-imidazol-5-yl]methylene]-1,3-dioxo-, methyl ester, (Z)

A mixture of glycine methyl ester hydrochloride (0.77 g, 6.17 mmol), homophthalic anhydride (1.0 g, 6.17 mmol) and K$_2$CO$_3$ (0.86 g) in toluene (60 mL) was heated under reflux with a Dean-Stark apparatus for 8 hours. The reaction mixture was cooled, filtered, and the residue was washed thoroughly with EtOAc. The filtrate and the washings were evaporated to give 1.15 g of a yellow solid. MS (EI) 233 (m). This was used as is for the next step.

A mixture of 0.75 g (2.62 mmol) of the aldehyde from Example 11B and 0.6 g (2.62 mmol) of the above-homophthalimide-derivative in toluene (50 mL) containing catalytic amount of piperidine was heated under reflux for 18 hours. Toluene was distilled under vacuum and the residue chromatographed (CH$_2$Cl$_2$/Acetone 2–7%) to give 0.9 g of a bright orange solid. 1H NMR indicate 95% of the Z-isomer. MS (CI) 502, (m).

Analysis calculated for C$_{28}$H$_{27}$N$_3$O$_6$: C, 67.06; H, 5.43; N, 8.58. Found: C, 67.07; H, 5.37; N, 8.22.

EXAMPLE 9

(Z)-3-[[3-[(4-carboxyphenyl)methyl]-2-propyl-3H-imidazol-4-yl]methylene]-2,3-dihydro-2-oxo-1H-indole-1-acetic acid (E)-3-[[3-[(4-carboxyphenyl)methyl]-2-propyl -3H-imidazol-4-yl]methylene]-2,3-dihydro-2-oxo-1H-indole-1-acetic acid A solution of 0.26 g (1.36 mmol) of 2,3-dihydro-2-oxo-1H-indole-1-acetic acid (prepared by saponification of 2,3-dihydro-2-oxo-1H-indole-1-acetic acid, ethyl ester) and 0.37 g (1.36 mmol) of compound from Example 11C in (5 mL) of acetic acid containing 10 mg of β-alanine was refluxed for 18 hours. The solution was cooled and the precipitate was filtered. The residue was washed with hexane and subjected to fractional crystallization from isopropyl alcohol to give E - and Z - isomers. Z - isomer; orange sol id; mp 290°–291° C. (dec). MS (CI) 446 (m).

Analysis calculated for C$_{25}$H$_{23}$N$_3$O$_5$.0.53 H$_2$O: C, 65.99; H, 5.33; N, 9.33. Found: C, 65.60; H, 4.74; N, 8.96.

E-isomer; yellow solid, mp 198°–200° C. MS (CI) 446 (m). Analysis calculated for C$_{25}$H$_{23}$N$_3$O$_5$.0.9 H$_2$O: C, 65.04; H, 5.41; N, 9.10. Found: C, 64.88; H, 5.44, N, 9.06.

EXAMPLE 10

Benzoic acid, 4-[[2-butyl-5-[(2,3-dihydro-2-oxo-1H-indol-3-yl)methyl]-1H-imidazol-1-yl]methyl]-, methyl ester, (±)

A solution of (0.5 g) of the compound from Example 2E in AcOH (15 mL) containing Ra/Ni (0.5 g) was subjected to catalytic reduction. HOAc was distilled under high vacuum and the residue was taken up in EtOAc. The EtOAc solution was washed with NaHCO$_3$ followed by water, dried, and evaporated to yield an off-white foam. It was chromatographed (CH$_2$Cl$_2$/MeOH, 5–10%) to give 0.29 g of the desired title compound. MS (CI) 417 (m).

Analysis calculated for C$_{25}$H$_{27}$N$_3$O$_3$.0.5 H$_2$O: C, 70.40; H, 6.62; N, 9.85. Found: C, 70.04; H, 6.47; N, 9.62.

Synthesis of the requisite 5-formyl-imidazole derivatives.

EXAMPLE 11

Ethyl 2-butyl-4-[[5-(formyl)-1H-imidazol-1-yl]methyl]benzoate was prepared according to the procedure described in U.S. Pat. No. 4,207,324.

2-Butyl-4-chloro-5-formyl-imidazole

A mixture of 2-butyl-4-chloro-5-hydroxymethylimidazole 20 g (0.1 mol) and MnO$_2$ (46.1 g, 0.53 mol) in THF (500 mL) was heated at reflux for 4 hours. The reaction mixture was cooled and filtered through a bed of celite and washed thoroughly with hot THF. The filtrate and the washings were concentrated under reduced pressure to give 18.7 g of a solid. It was chromatographed using CH$_2$Cl$_2$/MeOH (2%) as eluant to give 14 g of a solid; mp 95°–96° C.

A mixture of the above aldehyde (1.86 g, 0.01 mol) and CS$_2$CO$_3$ (7.17 g, 0.02 mol) in DMF (20 mL) was stirred for 10 minutes. To this mixture was added a solution of (4-carbethoxy) benzylbromide (2.7 g, 0.011 mol) in DMF (10 mL) and the resulting mixture was stirred for 2 hours. DMF was distilled, the residue was treated with water, and the mixture was extracted with EtOAc. The EtOAc solution was washed with brine, dried, and evaporated. The residue was chromatographed (CH$_2$Cl$_2$/EtOAc, 10–15%) to give an oil (2.7 g). MS (CI) 345 (m).

Analysis calculated for C$_{18}$H$_{21}$ClN$_2$O$_3$: C, 61.98; H, 6.07; N, 8.03. Found: C, 61.65; H, 6.09; N, 7.84.

A solution of the above 4-chloro-imidazole derivative (1.18 g) in EtOH (75 mL) containing KOAc (0.33 g) was subjected to catalytic reduction in presence of 5% Pd-C to give the title compound as an oil (0.8 g). MS (CI) 314, (m).

The following compounds were prepared in an analogous manner.

EXAMPLE 11A

Methyl 2-butyl-4-[[5-(formyl)-1H-imidazol-1-yl]methyl]benzoate

EXAMPLE 11B

Methyl 2-propyl-4-[[5-(formyl)-1H-imidazol-1-yl]methyl]benzoate

EXAMPLE 11C

2-Propyl-4-[[5-(formyl)-1H-imidazol-1-yl]methyl]-benzoic acid was obtained from 11B by saponification.

EXAMPLE 11D

Methyl 4-[[2-ethyl-5-(formyl)-4-methyl-1H-imidazol-1-yl]methyl]benzoate

Methyl 4-[[2-ethyl-4-methyl-1H-imidazol-1-yl]methyl]benzoate compound was prepared from 2-ethyl-4-methyl-imidazole and (4-carbmethoxy) benzylbromide in an analogous fashion as described in Example 11. A solution of the above imidazole (2.17 g, 8.14 mmol), NaOAc (1.17 g), 37 % HCHO (10 mn), and AcOH (1.2 mn) was heated under reflux for 22 hours. The solution was evaporated under vacuo, and the residue was stirred with 10 mL of 20% NaOH solution for 2 hours. It was diluted with water and the solution was extracted with CH$_2$Cl$_2$. The extract was washed with water, dried, and evaporated to an oil. It was chromatographed (CH$_2$Cl$_2$/MeOH, 2–5%) to give 1.0 g of the desired hydroxymethyl compound as a foam. MS (CI 288 (m).

A solution of the above hydroxymethyl imidazole derivative (1.0 g) was oxidized with MnO$_2$ (1.5 g) in CH$_2$Cl$_2$ (10 mL) as before. The product was purified by chromatography (CH$_2$Cl$_2$/MeOH, 2%) to give the title compound (0.73 g) as a highly viscous gum which crystallized on standing, MS (CI) 286 (m).

EXAMPLE 11E

2-Ethyl-4-[[5-(formyl)-1H-imidazol-1-yl]methyl]benzoic acid

A solution of the above ester from Example 11D in MeOH (4 mL) and 4N KOH (1.3 mL) was stirred at room temperature for 18 hours. MeOH was removed, the residue was treated with water, and the solution was adjusted to pH 5. It was extracted with EtOAc and the extract was dried and evaporated to give a pale yellow solid which was used as is for condensation with oxindole.

EXAMPLE 12

Ethyl 4-[[5-formyl-2-propyl-4-(1H-pyrrol-1-yl)-1H imidazol-1-1-yl]methyl]benzoate Ethyl 4-amino-2-propylimidazole-5-carboxylate A mixture of methyl propionimidate hydrochloride (4.8 g), ethyl 2-amino-2-cyanoacetate oxalate (4.0 g), anhydrous sodium acetate (9.1 g), and absolute ethanol (75 mL) was stirred at room temperature for 18 hours. Solids were removed by filtration and the filtrate was evaporated. The residue was partitioned between ethyl acetate and water. The ethyl acetate layer was washed with saturated NaCl, dried over MgSo4, and evaporated. Flash chromatography on silica gel, eluting with a gradient of dichloromethane-ethyl acetate (75:25) to ethyl acetate gives the title compound (2.7 g) as a pale yellow solid, mp 111°–114° C.; MS (DEI) 211 (m).

Ethyl 2-propyl-4-(1H-pyrrol-1-yl)imidazole-5-carboxylate

A solution of ethyl 4-amino-2-propylimidazole-5-carboxylate from above (9.34 g, 47 mmol) and sodium acetate (23.2 g) in acetic acid (100 mL) was heated to reflux and treated with 2,5-dimethoxy-tetrahydrofuran (6.75 mL, 52 mmol). The reaction was held at reflux for 30 minutes, then cooled back to room temperature with an ice bath. The majority of the acetic acid was evaporated under reduced pressure, then the residue was partitioned between ethyl acetate and 10% aqueous $K_2CO_3$ (120 mL) each. The organic layer was dried over $MgSO_4$ and evaporated. The residue was purified by flash chromatography on silica gel, eluting with $CH_2Cl_2$-ethyl acetate (80:20). Evaporation of solvents gave a solid which was recrystallized from hexane/EtOAc (1:1) to give 7.4 g of the title compound, mp 134°–135° C.; MS (CI), 248 (m +1).

2-Propyl-5-(1H-pyrrol-1-yl)-1H-imidazole-4-methanol

Dissolved 11.77 mM (2.91 g) of the imidazole ester compound from above in 60 mL of dry THF followed by dropwise addition of 12 mL of 1 M lithium aluminum hydride in ether over a period of 20 minutes. The resulting reaction was allowed to stir overnight at room temperature. The reaction mixture was treated with 20 mL saturated aqueous ammonium sulfate resulting in a solid white precipitate which was filtered and washed well with ethyl acetate. The filtrate and the washings were then washed with water, brine, and then dried over $MgSO_4$. Filtering off the drying agent and evaporating off the solvent gave a white solid which was crystallized from an 8:1 mixture of heptane and ethyl acetate to give 1.48 g (61.4%) of a white solid, mp 155°–158° C.; MS (CI) 205 (m).

2-propyl-5-(1H-pyrrol-1-yl)-1H-imidazole-4-carboxaldehyde

Dissolved 6.63 mM (1.36 g) of the imidazole alcohol compound in 60 mL of THF, followed by addition of 2.87 g (5 eq) of activated manganese dioxide while stirring vigorously. The resulting black suspension was heated to reflux for 5 hours then filtered warm through a pad of celite. The solids were washed well with ethyl acetate resulting in a yellow filtrate that when evaporated gave a beige solid. This crude solid was recrystallized from hexane/ethyl acetate (10:1) to give 0.74 g (54.9%) of a white solid, mp 118.5°–10° C.

Analysis calculated for $C_{11}H_{13}N_3O$: C, 65.01; H, 6.45; N, 20.67. Found: C, 64.92; H, 6.29; N, 20.30. MS (CI) 203 (m).

By substituting the 5-formyl-imidazole compound in Example 11 with the above 5-formyl-imidazole and following the procedure described in Example 11, the title compound was obtained as an oil, MS (CI) 351 (m).

EXAMPLE 13

5-[4-(Bromomethyl)phenyl]-2-(triphenylmethyl)-2H-tetrazole 5-(4-Methylphenyl)-1H-tetrazole A solution of 4-toluenitrile (52.09 g, 0.44 mol), $NaN_3$ (57.8 g 0.87 mol) and $NH_4Cl$ (47.62 g, 0.89 mol) in DMF (150 mL) was heated at 95° C. for 18 hours. The reaction mixture was cooled, diluted with water, and acidified with HCl. The solid was filtered, washed with water, and dried under vacuum at 70° C. for 4 hours to give the title compound; mp 243°–244° C.; MS (CI) 161 (m +1).

5-(4-Methylphenyl)-2-(triphenylmethyl)-2H-tetrazole

Tritylchloride (112.4 g, 0.4 mol) was added to a solution of the above tetrazole (68 g, 0.4 mol) and $Et_3N$ (61.4 g, 0.44 mol) in DMF (2500 mL) with stirring. The reaction mixture was stirred for 16 hours and filtered. The residue was thoroughly washed with DMF. The filtrate and the washings were evaporated under vacuum and the residue was taken up in large volume of EtOAc. The EtOAc solution was washed with water, dried, and evaporated to give 165 g of the desired compound; mp 172°–175° C.

5-[4-(Bromomethyl)phenyl]-2-(triphenylmethyl)-2H-tetrazole

A mixture of the above compound (100 g, 0.248 mol) and NBS (44.2 g, 0.24 mol) in $CCl_4$ (1 L) containing catalytic amount of VAZO-52 (0.5 g) was heated under reflux for 4 hours. Additional quantity of NBS (4.4 g) was added and the reaction mixture was heated for 45 minutes. It was filtered and the filtrate was evaporated to give an orange solid. It was recrystallized from EtOAc/Hexane (2:1) to give 68 g of the title compound as a white solid, mp 165°–172 ° C.

Analysis calculated for $C_{27}H_{21}BrN_4$: C, 67.37; H, 4.40; N, 11.64. Found: C, 66.90; H, 4.20; N, 11.13.

EXAMPLE 14

2-Butyl-5-chloro-3-[[4-[2-(triphenylmethyl)-2H-tetrazol-5-yl]phenyl]methyl]-3H-imidazole-4-carboxaldehyde The bromomethyl derivative from Example 13 was used to alkylate 2-butyl-4-chloro-5-formyl-imidazole by following the procedure described in Example 11 to give the desired compound as a white solid (23 g); mp 154°–157° C., MS (CI), 587 (m −1);

Analysis calculated for $C_{35}H_{32}N_6ClO$: C, 71.48; H, 5.48; N, 14.29. Found: C, 71.36; H, 5.21; N, 14.15.

2-Butyl-3-[[4-[2-(triphenylmethyl)-2H-tetrazol-5-yl]phenyl]methyl]-3H-imidazole-4-carboxaldehyde 17.3 g of the chloro compound was reduced in presence of 5% Pd-C as described in Example 11. The crude material was purified via chromatography [CH$_2$Cl$_2$/Hexane (20%) CH$_2$Cl$_2$/EtOAc(20%)] to give the desired material; mp 176°–177° C.; MS (CI), 554 (m);

Analysis calculated for C$_{35}$H$_{34}$N$_6$O; C, 75.92; H, 6.01; N, 15.18. Found: C, 75.83; H, 5.97; N, 15.26.

EXAMPLE 15

The oxindoles were either commercially available or were prepared by following known literature methods.

1,3-Dihydro-1-propyl-2H-indol-2-one (Walker, et al, *J Med Chem* 1970;13:983–85).

2,3-Dihydro-N-methyl-2-oxo-1H-indole-1-carboxamide, mp 159°–162° C.

2,3-Dihydro-2-oxo-1H-indole-7-acetic acid, ethyl ester, mp 145°–146° C.

1,3-Dihydro-1-methyl-2H-indol-2-one.

1,3-Dihydro-1-(1-methylethyl)-2H-indol-2-one; waxy solid.

Analysis calculated for C$_{11}$H$_{13}$NO: C, 75.40; H, 7.48; N, 7.99. Found: C, 75.60; H, 7.46; N, 7.45. (Andreani, et al, *Fffarmaco Ed Sci* 1977;32:703–05).

1-Hydroxyoxindole; mp 198°–202° C. prepare by the literature procedure (Kende AS, Thurston J, *Syn Comm* 1990;20:2133).

2,3-Dihydro-2-oxo-1H-indole-1-acetic acid, ethyl ester.

EXAMPLE 16

(Z) Ethyl 3-[[2-butyl-1-[[4-(methoxycarbonyl)phenyl]methyl]-1H-imidazol-5-yl]methylene]-2,3-dihydro-2-oxo-1H-indole-1-acetate A mixture of 1 g of 2-butyl imidazole-4-carboxaldehyde and 2,3-dihydro-2-oxo-1H-indole-7-acetic acid, ethyl ester (1.5 g) in toluene (20 mL) containing 0.6 mL of piperidine was heated under reflux for 18 hours. Toluene was distilled under vacuum and the residue was crystallized from hexane/ethyl acetate to give 2.0 g of the desired product; mp 118°–119° C., MS (CI), 354 (m);

Analysis calculated for C$_{20}$H$_{23}$N$_3$O$_3$; C, 667.97; H, 6.56; N, 11.89. Found: C, 68.15; H, 6.62; N, 12.07.

BOC anhydride (1.9 g, 8.7 mmol) was added to a solution of the above imidazole product (2.0 g, 5.6 mmol) and Et$_3$N (6.2 mmol) in CH$_2$Cl$_2$ (20 mL) and the reaction mixture was stirred at room temperature for 16 hours. The solution was washed with water, brine, and dried over anhydride MgSO$_4$, and stripped to give a solid which was recrystallized from hexane/EtOAc to give a yellow solid. MS (CI), 454 (m);

Analysis calculated for C$_{25}$H$_{31}$N$_3$O$_5$.0.4 H$_2$O; C, 65.17; H, 6.96; N, 9.12. Found: C, 65.31; H, 6.79; N, 8.72.

To a solution of triflic anhydride (0.74 mL, 4.4 mmol) in CH$_2$Cl$_2$ (20 mL) at −78° C. was added dropwise a solution of 4-(carbomethoxy)benzylalcohol (0.7 g, 4.2 mmol) and diisopropyl ethylamine (0.8 mL, 4.6 mmol) in CH$_2$Cl$_2$ (10 mL) under nitrogen atmosphere. The mixture was stirred for additional 15 minutes followed by the addition of a solution of the above BOC imidazole derivative (1.9 g, 4.2 mmol) in CH$_2$Cl$_2$ (10 mL). The solution was allowed to warm to room temperature and stirred for 16 hours. The solution was diluted with CH$_2$Cl$_2$ and washed with water, brine, dried over anhydrous MgSO$_4$, and stripped. The residue was dissolved in CH$_2$Cl$_2$ and filtered to give 0.43 g of the title product; mp 207°–209° C.; MS (CI), 502 (m): The filtrate was chromatographed (EtOAc/CH$_2$Cl$_2$ (4:1)—EtOAc) to give 0.9 g of additional product. This was identical to the compound from Example 2A.

EXAMPLE 17

Ethyl 3-[[2-butyl-1-[[4-[1H-tetrazol-5-yl]phenyl]methyl]-1H-imidazol-5-yl]methylene]2,.3-dihydro-2-oxo-1H-indole-1-acetate A mixture of 2.0 g of 5-[4-(bromomethyl)phenyl]-2-(triphenylmethyl)-2H-tetrazole from Example 13 and 1N NaOH (5 mL) in THF (20 mL) was stirred for 24 hours. The solvent was evaporated and the aqueous solution extracted with EtOAc. The organic layer was washed with water, dried, and evaporated to give 1.8 g of 5-[4-(hydroxymethyl)phenyl]-2-(triphenylmethyl)-2H-tetrazole which was used as is for the next step; MS (EI), 418 (m).

By following the procedure described in Example 16 and using the above 5-[4-(hydroxymethyl) phenyl]-2-(triphenylmethyl)-2H-tetrazole in place of 4-(carbomethoxy)benzyl alcohol, the compound ethyl 3-[[2-butyl-3-[[4-[2-(triphenylmethyl)-2H-tetrazol-5-yl]phenyl]methyl]-3H-imidazol-4-yl]methylene]-2,3-dihydro-2-oxo-1H-indole-1-acetate was obtained.

To a solution of triflic anhydride (0.74 mL, 4.4 mmol) in CH$_2$Cl$_2$ (20 mL) at −78° C. was added dropwise a solution of 5-[4-(hydroxymethyl)phenyl]-2-(triphenylmethyl)-2H-tetrazole (1.75 g, 4.2 mmol) and diisopropyl ethylamine (0.8 mL, 4.6 mmol) in C$_2$Cl$_2$ (10 mL) under nitrogen atmosphere. The mixture was stirred for additional 15 minutes followed by the addition of a solution of the BOC imidazole derivative from Example 16 (1.9 g, 4.2 mmol) in CH$_2$Cl$_2$ (10 mL). The solution was allowed to warm to room temperature and stirred for 16 hours. The solution was diluted with CH$_2$Cl$_2$ and washed with water, brine, dried over anhydrous MgSO$_4$, and stripped. The residue was dissolved in CH$_2$Cl$_2$ and filtered to give 1.7 g of the title product; MS (FAB), 755 (m).

A solution of the above material (1.7 g) in CH$_3$OH (15 mL) and citric acid (10%, 5 mL) was heated at reflux for 16 hours. The solution was evaporated and the CH$_3$OH solution was diluted with water and extracted with hexane. The aqueous solution was finally extracted with EtOAc and the extract was washed with water, dried over MgSO$_4$, stripped, and the residue chromatographed (CH$_2$Cl$_2$/MeOH; 9:1) to give 0.8 g of the title compound; MS (FAB), 512 (m +1);

Analysis calculated for C$_{28}$H$_{29}$N$_7$O$_3$.0.51 EtOAc.0.63 H$_2$O; C, 63.55; H, 6.11; N, 17.24. Found: C, 63.54; H, 5.81; N, 17.23.

We claim:

1. A compound of formula

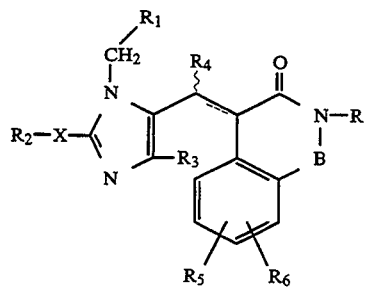

or a pharmaceutically acceptable salt thereof wherein $R_1$ is adamantylmethyl,
phenyl,
biphenyl, or
naphthyl, each of which is unsubstituted or substituted by one to three substituents selected from
Cl,
Br,
F,
I,
alkyl of from one to four carbon atoms,
nitro,
tetrazol-5-yl,
alkoxy of from one to four carbon atoms,
hydroxy,
$SO_3H$,
$SO_2$alkyl of from one to four carbon atoms,
CN,
$C_nF_{2n+1}$ wherein n is an integer of from 1 to 3,
$CO_2R_4$,
$SO_2NHR_4$,
$NHSO_2R_4$,
$NHSO_2C_nF_{2n+1}$,
$CON(R_4)_2$ wherein $R_4$ is hydrogen or lower alkyl;

X is a single bond, S, or O;

$R_2$ is alkyl of from two to ten carbon atoms, alkenyl of from two to ten carbon atoms, alkynyl of from three to ten carbon atoms, cycloalkyl of from three to six carbon atoms,
$(CH_2)_m$phenyl wherein m is an integer of from zero to eight and phenyl is unsubstituted or substituted by one to three substituents selected from alkyl of from one to four carbon atoms,
nitro,
Cl,
Br,
F,
I,
hydroxy,
alkoxy of from one to four carbon atoms, or
$NR_4R_4$ wherein $R_4$ is as defined above;

$R_3$ is hydrogen,
Cl,
Br,
F,
I,
CHO,
hydroxymethyl,
alkyl,
aryl,
heteroaryl,
$CO_2R_4$,
$CONR_4R_4$,
$NO_2$, or
$C_nF_{2n+1}$ wherein n is as defined above;

$R_4$ is hydrogen or alkyl of from one to five carbon atoms,

R is hydrogen or alkyl of from one to five carbon atoms which alkyl is unsubstituted or substituted with
CN,
$CO_2R_4$,
tetrazol-5-yl,
$CONHR_4$,
$CONH(CH_2)_nCO_2R_4$,
phenyl unsubstituted or substituted by one to three substituents selected from alkyl of from one to four carbon atoms,
nitro,
Cl,
F,
I,
hydroxy,
alkoxy of from one to four carbon atoms, or
$NR_4R_4$ wherein $R_4$ is as defined above; or R is $OR_4$, or $O(CH_2)_n CO_2R_4$;

$R_5$ and $R_6$ are each independently
hydrogen,
halogen,
alkyl of from one to five carbon atoms,
alkyloxy of from one to five carbon atoms,
$NO_2$,
$NHCOR_4$,
$NHSO_2R_4$,
$(CH_2)_nCO_2R_4$ wherein n and $R_4$ are as defined above; and B is a bond;

the is a double or single bond; and the indicates both E and Z isomer of the compound.

2. A compound according to claim 1 wherein:

$R_1$ is phenyl
biphenyl, or
naphthyl, each of which is unsubstituted or substituted by one to three substituents selected from
Cl,
F,
alkyl of from one to four carbon atoms,
nitro,
tetrazol-5-yl,
alkoxy of from one to four carbon atoms,
hydroxy,
$SO_3H$,
CN,
$C_nF_{2n+1}$ wherein n is an integer of from 1 to 3,
$CO_2R_4$,
$SO_2NHR_4$,
$NHSO_2R_4$,
$CONR_4R_4$ wherein $R_4$ is hydrogen or lower alkyl;

X is a single bond or S;

$R_2$ is alkyl of from two to eight carbon atoms, or cycloalkyl of from three to six carbon atoms;

$R_3$ is hydrogen,
Cl,
F,
I,
CHO,
hydroxymethyl,
alkyl,
aryl,
pyrrole,
$CO_2R_4$, CONR$_4$R$_4$,
NO$_2$, or
C$_n$F$_{2n+1}$ wherein n is as defined above;
R$_4$ is hydrogen or alkyl of from one to four carbon atoms,
R is hydrogen or alkyl of from one to four carbon atoms unsubstituted or substituted with
CO$_2$R$_4$,
tetrazol-5-yl,
CONHR$_4$,
CONHR$_4$ wherein R$_4$ is as defined above;
R$_5$ and R$_6$ are each independently
hydrogen,
alkyl of from one to four carbon atoms,
alkyloxy of from one to four carbon atoms,
NO$_2$,
NHCOR$_4$,
NHSO$_2$R$_4$,
(CH$_2$)$_n$CO$_2$R$_4$ wherein n and R$_4$ are defined above,
B is a bond, and
The ⋮ is a double or single bond.

3. A compound according to claim 1 wherein:
R$_1$ is phenyl substituted by one to three substituents selected from
Cl,
F,
trifluoromethyl,
nitro,
methyl,
methoxy,
hydroxy,
sulfonamido,
carboxy,
carboC$_1$-C$_4$alkoxy,
carbamoyl,
CN, or
tetrazol-5-yl;
X is a single bond;
R$_2$ is alkyl of from two to eight carbon atoms;
R$_3$ is hydrogen;
R$_4$ is hydrogen;
R is CH$_2$CO$_2$R$_4$ wherein R$_4$ is hydrogen or lower alkyl;
R$_5$ is alkyl of from one to four carbon atoms or alkoxy of from one to four carbon atoms;
R$_6$ is hydrogen;
B is a bond; and
The ⋮ is a double bond.

4. A pharmaceutical composition for treating hypertension in mammals comprising an antihypertensive amount of a compound of formula I

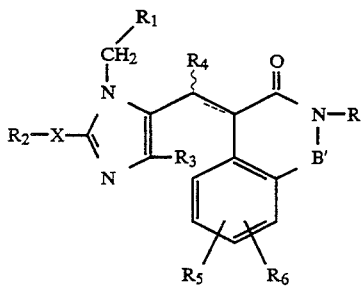

or a pharmaceutically acceptable salt thereof wherein
R$_1$ is adamantylmethyl,
phenyl,
biphenyl, or
naphthyl, each of which is unsubstituted or substituted by one to three substituents selected from the group consisting of
Cl,
Br,
F,
I,
alkyl of from one to four carbon atoms,
nitro,
tetrazol-5-yl,
alkoxy of from one to four carbon atoms,
hydroxy,
SO$_3$H,
SO$_2$alkyl of from one to four carbon atoms,
CN,
C$_n$F$_{2n+1}$ wherein n is an integer of from 1 to 3,
CO$_2$R$_4$,
SO$_2$NHR$_4$,
NHSO$_2$R$_4$,
NHSO$_2$C$_n$F$_{2n+1}$,
CON(R$_4$)$_2$ wherein R$_4$ is hydrogen or lower alkyl;
X is a single bond, S, or O;
R$_2$ is alkyl of from two to ten carbon atoms,
alkenyl of from two to ten carbon atoms,
alkynyl of from three to ten carbon atoms,
cycloalkyl of from three to six carbon atoms,
(CH$_2$)$_m$phenyl wherein m is an integer of from zero to eight and phenyl is unsubstituted or substituted by one to three substituents selected from the group consisting of alkyl of from one to four carbon atoms,
nitro,
Cl,
Br,
F,
I,
hydroxy,
alkoxy of from one to four carbon atoms, or
NR$_4$R$_4$ wherein R$_4$ is as defined above;
R$_3$ is hydrogen,
Cl,
Br,
F,
I,
CHO,
hydroxymethyl,
straight or branched alkyl of from 1–10 carbon atoms,
aryl selected from the group consisting of phenyl, 1-naphthyl and 2-naphthyl,
CO$_2$R$_4$,
CONR$_4$R$_4$,
NO$_2$, or
C$_n$F$_{2n+1}$ wherein n is as defined above;
R$_4$ is hydrogen or alkyl of from one to five carbon atoms,
R is hydrogen or alkyl of from one to five carbon atoms which alkyl is unsubstituted or substituted with
CN,
CO$_2$R$_4$,
tetrazol-5-yl,
CONHR$_4$,
CONH(CH$_2$)$_n$CO$_2$R$_4$,
phenyl unsubstituted or substituted by one to three substituents selected from alkyl of from one to four carbon atoms, nitro,
Cl,
F,
I,
hydroxy,
alkoxy of from one to four carbon atoms, or NR$_4$R$_4$ wherein R$_4$ is as defined above; or
R is OR$_4$, or O(CH$_2$)$_n$ CO$_2$R$_4$;
R$_5$ and R$_6$ are each independently
hydrogen,
halogen,
alkyl of from one to five carbon atoms,
alkyloxy of from one to five carbon atoms,
NO$_2$,
NHCOR$_4$,
NHSO$_2$R$_4$,
(CH$_2$)$_n$CO$_2$R$_4$ wherein n and R$_4$ are as defined above; and
B' is a bond;
the is a double or single bond; and the indicates both E and Z isomer of the compound together with a pharmaceutically acceptable carrier.

5. A method for treating hypertension in a mammal suffering therefrom comprising administering to said mammal an antihypertensive effective amount of a composition according to claim 4.

6. A pharmaceutical composition for treating congestive heart failure comprising a therapeutically effective amount of a compound of formula I

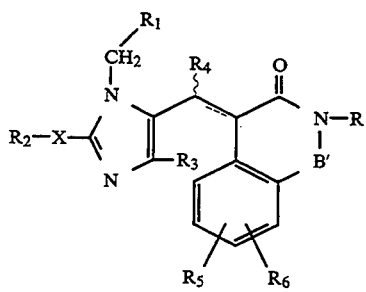

I or a pharmaceutically acceptable salt thereof wherein
R$_1$ is adamantylmethyl,
phenyl, or
naphthyl, each of which is unsubstituted or substituted by one to three substituents selected from the group consisting of
Cl,
Br,
I,
alkyl of from one to four carbon atoms,
nitro,
tetrazol-5-yl,
alkoxy of from one to four carbon atoms,
hydroxy,
SO$_3$H,
SO$_2$alkyl of from one to four carbon atoms,
CN,
C$_n$F$_{2n+1}$ wherein n is an integer of from 1 to 3,
CO$_2$R$_4$,
SO$_2$NHR$_4$,
NHSO$_2$R$_4$,
NHSO$_2$C$_n$F$_{2n+1}$,
CON(R$_4$)$_2$ wherein R$_4$ is hydrogen or lower alkyl;
X is a single bond, S, or O;
R$_2$ is alkyl of from two to ten carbon atoms,
alkenyl of from two to ten carbon atoms,
alkynyl of from three to ten carbon atoms,
cycloalkyl of from three to six carbon atoms,
(CH$_2$)$_m$phenyl wherein m is an integer of from zero to eight and phenyl is unsubstituted or substituted by one to three substituents selected from the group consisting of alkyl of from one to four carbon atoms,
nitro,
Cl,
Br,
F,
hydroxy,
alkoxy of from one to four carbon atoms, or NR$_4$R$_4$ wherein R$_4$ is as defined above;
R$_3$ is hydrogen,
Cl,
Br,
F,
I,
CHO,
hydroxymethyl,
a straight or branched alkyl of from 1-10 carbon atoms,
aryl selected from the group consisting of phenyl, 1-naphthyl and 2-naphthyl,
CO$_2$R$_4$,
CONR$_4$R$_4$,
NO$_2$, or
C$_n$F$_{2n+1}$ wherein n is as defined above;
R$_4$ is hydrogen or alkyl of from one to five carbon atoms,
R is hydrogen or alkyl of from one to five carbon atoms which alkyl is unsubstituted or 'substituted with
CN,
CO$_2$R$_4$,
tetrazol-5-yl,
CONHR$_4$,
CONH(CH$_2$)$_n$CO$_2$R$_4$,
phenyl unsubstituted or substituted by one to three substituents selected from alkyl of from one to four carbon atoms,
nitro,
Cl,
F,
I,
hydroxy,
alkoxy of from one to four carbon atoms, or NR$_4$R$_4$ wherein R$_4$ is as defined above; or
R is OR$_4$, or O(CH$_2$)$_n$ CO$_2$R$_4$;
R$_5$ and R$_6$ are each independently
hydrogen,
halogen,
alkyl of from one to five carbon atoms,
alkyloxy of from one to five carbon atoms,
NO$_2$,
NHCOR$_4$,
NHSO$_2$R$_4$,
(CH$_2$)$_n$CO$_2$R$_4$ wherein n and R$_4$ are as defined above; and
B' is a bond;
the is a double or single bond; and the indicates both E and Z isomer of the compound in admixture with a pharmaceutically acceptable carrier.

7. A method of treating congestive heart failure comprising administering to a host suffering therefrom a therapeutically effective amount of a composition according to claim 6 in unit dosage form.

* * * * *

UNITED STATES PATENT AND TRADEMARK OFFICE
CERTIFICATE OF CORRECTION

PATENT NO. : 5,389,661
DATED : February 14, 1995
INVENTOR(S) : Sircar et al

It is certified that error appears in the above-indentified patent and that said Letters Patent is hereby corrected as shown below:

Column 40, line 34, after the first "the" insert "———".

Column 40, line 34, after the second "the" insert "∿".

Column 41, line 21, after "The" insert "———".

Column 41, line 48, after "The" insert "———".

Column 42, line 44, move "F," to properly vertically align.

Column 42, line 48, at the beginning of the line insert "a".

Column 43, line 19, after the first "the" insert "———".

Column 43, line 19, after the second "the" insert "∿".

Column 43, line 45, after "phenyl," insert -- biphenyl, --.

Column 43, line 50, after "Br," on a line by itself, insert -- F, --.

Column 44, line 11, after "F," on a line by itself, insert -- I, --.

Column 44, line 32, delete the apostrophe before the word "substituted".

UNITED STATES PATENT AND TRADEMARK OFFICE
CERTIFICATE OF CORRECTION

PATENT NO. : 5,389,661
DATED : February 14, 1995
INVENTOR(S) : Sircar et al

It is certified that error appears in the above-indentified patent and that said Letters Patent is hereby corrected as shown below:

Column 44, line 60, after the first "the" insert "═══".

Column 44, line 60, after the second "the" insert "∿".

Signed and Sealed this

Eighth Day of August, 1995

BRUCE LEHMAN

*Attest:*

*Attesting Officer*          *Commissioner of Patents and Trademarks*